(12) United States Patent
Pavlovskaia et al.

(10) Patent No.: US 7,040,896 B2
(45) Date of Patent: *May 9, 2006

(54) SYSTEMS AND METHODS FOR REMOVING GINGIVA FROM COMPUTER TOOTH MODELS

(75) Inventors: Elena Pavlovskaia, San Francisco, CA (US); Venkata S. Sarva, Fremont, CA (US); Carmen Cheang, Sunnyvale, CA (US)

(73) Assignee: Align Technology, Inc., Santa Clara, CA (US)

( * ) Notice: Subject to any disclaimer, the term of this patent is extended or adjusted under 35 U.S.C. 154(b) by 126 days.

This patent is subject to a terminal disclaimer.

(21) Appl. No.: 10/087,153

(22) Filed: Feb. 28, 2002

(65) Prior Publication Data

US 2002/0177108 A1    Nov. 28, 2002

Related U.S. Application Data

(63) Continuation-in-part of application No. 09/640,328, filed on Aug. 16, 2000, now Pat. No. 6,386,878.

(51) Int. Cl.
*A61C 5/00* (2006.01)

(52) U.S. Cl. ........................................ 433/215
(58) Field of Classification Search ................ 433/24, 433/213, 215; 345/424, 622
See application file for complete search history.

(56) References Cited

U.S. PATENT DOCUMENTS

| | | | |
|---|---|---|---|
| 2,467,432 A | 4/1949 | Kesling | |
| 3,407,500 A | 10/1968 | Kesling | |
| 3,600,808 A | 8/1971 | Reeve | |
| 3,660,900 A | 5/1972 | Andrews | |
| 3,683,502 A | 8/1972 | Wallshein | |
| 3,860,803 A | 1/1975 | Levine | |
| 3,861,044 A | 1/1975 | Swinson, Jr. | |
| 3,916,526 A | 11/1975 | Schudy | |
| 3,922,786 A | 12/1975 | Lavin | |
| 3,950,851 A | 4/1976 | Bergersen | |
| 4,014,096 A | 3/1977 | Dellinger | |
| 4,195,046 A | 3/1980 | Kesling | |
| 4,253,828 A | 3/1981 | Coles et al. | |
| 4,324,546 A | 4/1982 | Heitlinger et al. | |
| 4,324,547 A | 4/1982 | Arcan et al. | |
| 4,348,178 A | 9/1982 | Kurz | |
| 4,478,580 A | 10/1984 | Barrut | |
| 4,500,294 A | 2/1985 | Lewis | |
| 4,504,225 A | 3/1985 | Yoshii | |
| 4,505,673 A | 3/1985 | Yoshii | |
| 4,526,540 A | 7/1985 | Dellinger | |

(Continued)

FOREIGN PATENT DOCUMENTS

EP        0091876 A1    10/1983

(Continued)

OTHER PUBLICATIONS

Andrews, "The Six Keys to Optimal Occlusion" *Straight Wire, Chapter 3* pp. 13-24.

(Continued)

*Primary Examiner*—Todd E. Manahan
(74) *Attorney, Agent, or Firm*—Townsend and Townsend and Crew LLP

(57) ABSTRACT

A computer-implemented method separates gingiva from a model of a tooth by defining a cutting surface along the gingiva; and applying the cutting surface to the tooth to separate the gingiva from the tooth.

25 Claims, 16 Drawing Sheets

U.S. PATENT DOCUMENTS

| | | |
|---|---|---|
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,092,022 A * | 3/1992 | Duret .................. 29/896.1 |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,338,198 A | 8/1994 | Wu et al. |
| 5,340,309 A | 8/1994 | Robertson |
| 5,342,202 A | 8/1994 | Deshayes |
| 5,367,478 A | 11/1994 | Hattori |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,587,912 A | 12/1996 | Anderson et al. |
| 5,605,459 A | 2/1997 | Kuroda et al. |
| 5,607,305 A | 3/1997 | Andersson et al. |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,800,174 A | 9/1998 | Andersson |
| 5,866,058 A | 2/1999 | Batchelder et al. |
| 5,879,158 A | 3/1999 | Doyle et al. |
| 5,880,961 A | 3/1999 | Crump |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chisti et al. |
| 6,044,309 A | 3/2000 | Honda |
| 6,049,743 A | 4/2000 | Baba |
| 6,123,544 A | 9/2000 | Cleary |
| 6,183,248 B1 | 2/2001 | Chishti et al. |
| 6,190,165 B1 | 2/2001 | Andreiko et al. |
| 6,217,334 B1 | 4/2001 | Hultgren |

FOREIGN PATENT DOCUMENTS

| | | |
|---|---|---|
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 2369828 | 6/1978 |
| FR | 2369828 A1 | 6/1978 |
| FR | 2652256 A1 | 3/1991 |
| WO | WO 90/08512 A1 | 8/1990 |
| WO | WO 91/04713 A1 | 4/1991 |
| WO | WO 94/10935 | 5/1994 |
| WO | WO 94/10935 A1 | 5/1994 |
| WO | WO 98/32394 | 7/1998 |
| WO | WO 98/58596 | 7/1998 |
| WO | WO 98/44865 A1 | 10/1998 |
| WO | WO 98/58596 A1 | 12/1998 |

OTHER PUBLICATIONS

Biostar Opeation & Training Manual. Great Lakes Orthodontics, Ltd. 199 Fire Tower Drive, Tonawanda, New York. 14150-5890. 20 pages total.

Chiappone, "Constructing the gnathologic setup and positioner" *J. Clin. Orthod.* (1980) 14:121-133.

Cottingham, "Gnathologic clear plastic positioner" *Am. J. Orthod.* (1969) 55:23-31.

Cureton, "Correcting malaligned mandibular incisors with removable retainers" *J. Clin. Orthod.* (1996) 30:390-395.

Dent-X posted at http://www.dent-x.com/DentSim.htm Sep. 24, 1998, 6 pages ttoal.

Elasser, "Some observations on the history and uses of the Kesling positioner" *Am. J. Orthod.* (1950) 36:368-374.

Kamada et al., "Case reports on tooth positioners using LTV vinyl silicone rubber" *J. Nihon University School of Dentistry* (1984) 26(1):11-29.

Kamada et al., "Construction of tooth positioners with LTV vinyl silicone rubber and some case reports" *J. Nihon University School of Dentistry* (1982) 24(1):1-27.

Kesling, "Coordinating the predetermined pattern and tooth positioner with conventional treatment" *Am. J. Orthod. Oral. Surg.* (1946) 32:285-293.

Kesling, "The philosophy of the tooth positioning appliance" *Am. J. Orthod. Oral. Surg.* (1945) 31(6):297-304.

Kleemann et al., "The speed positioner" *J. Clin. Orthod.* (1996) 30:673-680.

Kunii et al., "Articulation Simulation for an Intelligent Dental Care System" *Displays* (1994) 15:181-188.

Kuroda et al., "Three-dimensional dental cast analyzing system using laser scanning" *Am. J. Orthod. Dentofac. Orthop.* (1996) 110:365-369.

Nahoum et al., "The vacuum formed dental contour appliance" *The New York State Dental Journal* (1964) 30(9):385-390.

*Nippon Dental Review* "New orthodontic device-dynamic positioner (D.P.)-1. Approach to the proposal of D.P. and transparent silicone rubber" (1980) 452:61-74.

*Nippon Dental Review* "New orthodontic device-dynamic positioner (D.P.)-II. Practical application and construction of D.P." (1980) 454:107-130.

*Nippon Dental Review* "New orthodontic device-dynamic positioner (D.P.)-III. Case reports of reversed occlusion" 1980) 457:146-164.

*Nippon Dental Review* "New orthodontic device-dynamic positioner (D.P.)-Case reports of reversed occlusion" (1980) 458:112-129.

Nishiyama et al., "A new construction of tooth repositioner by LTV vinyl silicone rubber" *J. Nihon University School of Dentistry* (1977) 19(2):93-102.

Cardinal Industrial Finishes, Powder Coatings information posted at http://www.cardinalpaint.com on Aug. 25, 2000, 2 pages total.

Proffit et al., "Contemporary Orthodontics" Second Edition, Chapter 15, pp. 470-533.

*Raintree Essix™ & ARS Materials, Inc.*, Raintree Essix™ Technical Magazine Table of Contents and Essix™ Applications, http://www.essix.com/magazine/default.html (Aug. 13, 1997) 7 pages total.

Richmond et al., "The development of the PAR Index (Peer Assessment Rating): reliability and validity" *European Journal of Orthodontics* (1992) 14:125-139.

Schroeder et al., Eds. *The Visual Toolkit*, Prentice Hall PTR, New Jersey (1998) Chapters 6, 8, and 9 (pp. 153-210, 309-354, and 355-428, respectively).

Shilliday, "Minimizing finishing problems with the mini-positioner" *Am. J. Orthod.* (1971) 59:596-599.

Warunek et al., "Clinical use of silicone elastomer applicances" *JCO* (1989) XXIII(10):694-700.

Warunek et al., "Physical and mechanical properties of elastomers in orthodontic positioners" *Am. J. Orthod. Dentofac. Orthop.* (1989) 95:388-400.

Wells, "Application of the positioner appliance in orthodontic treatment" *Am. J. Orthodont.* (1970) 58:351-366.

Doyle, "Digital Dentistry" *Computer Graphics World* (Oct. 2000) pp. 50-54.

Redmond et al., "Clinical implications of digital orthodontics" *American Journal of Orthodontics and Dentofacial Orthopedics* (2000) 117(2):240-242.

Alexander et al., "The DigiGraph Work Station Part 2, Clinical Management," *JCO* (Jul. 1990), pp. 402-407.

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607,1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty", NATO Symposium on Applications of Human Biostereometrics, Jul. 9-13, 1978, SPIE vol. 166, pp. 112-123.

Baumrind et al., Mapping the Skull in 3-D, Reprinted from the Journal, *California Dental Association*, vol. 48, No. 2 (1972 Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research*; vol. 67, Special Issue Mar. 9-13, 1988, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion In The Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Brandestini et al., "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7, Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am.*

*Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Femoral Prosthesis, A Stereophotogrammetric Evaluation," *Clinical Orthopaedics and Related Research*, No. 201 (Dec. 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner" *Am. J. Orthod.*, vol. 55, No. 1, (Jan. 1969),. pp. 23-31.

Crawford, "Computers in Dentistry: Part 1: CAD/CAM: The Computer Moves Chairside," "Part 2: F. Duret—A Man With A Vision," "Part 3: The Computer Gives New Vision-Literally," "Part 4: Bytes 'N Bites" The Computer Moves From The Front Desk To The Operatory, *Canadian Dental Journal*, vol. 54(9), , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic and Reconstructive Surgery*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Duret et al., "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisee," (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, vol. 36, No. 5, (May1950) pp. 368-374.

Faber et al., "Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery, "Abstract of Papers, *Journal of Dental Research*, vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery, " *JCO*, (Apr., 1989), pp. 262-268.

Heaven et al., "Computer-based Image Analysis of Artificial Root Surface Caries," Abstracts of Papers, *Journal of Dental Research*, vol. 70,Apr. 17-21, 1991, p. 528.

Hoffmann et al., "Role of Cephalometry for Planning of Jaw Orthopedics and Jaw Surgery Procedures," (Article Summary In English, article in German), *Informationen*, (Mar. 1991), pp. 375-396.

Huckins, "CAD-CAM Generated Mandibular Model Prototype from MRI Data," *AAOMS* 1999, p. 96.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO*, (Apr. 1988), pp. 478-479.

Jones et al., "An Assessment of the Fit of a Parabolic Curve to Pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.*, vol. 63, No. 11 (Nov. 1984), pp. 1298-1301.

Kesling, "Coordinating the Predetermined Pattern and Tooth Positioner With Conventional Treatment" *Am. J. Orthod. Oral. Surg.*, 32:285-293, 1946.

Kesling, "The Philosophy of the Tooth Positioning Appliance" *Am. J. Orthod. Oral. Surg.*, 31(6):297-304, 1945.

Kleemann et al., "The Speed Positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop.* 44, 370-376 (Nr. 5), 1983.

McCann, "Dental Technology", Inside the ADA, *JADA.*, vol. 118 (Mar. 1989) pp. 286-294.

McNamara et al., "Invisible Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro, "*Schwizerische Monatsshrift fur Zahnmedizin*, vol. 85 (1985), p. 1118-1129.

Nahoum, "The Vacuum Formed Dental Contour Appliance" *The New York State Dental Journal*, 30(9):385-390, Nov. 1964.

Nash, "Cerec CAD/CAM Inlays: Aesthetics and Durability in a Single Appointment," *Dentistry Today*, (Oct. 1990), pp. 20, 22-23, 54.

Nishiyama et al., "A New Construction Of Tooth Repositioner By LTV Vinyl Silicone Rubber" J. Nihon University School of Dentistry, 19(2):93-102, 1977.

Pinkham, "Foolish' Concept Propels Technology," *Dentist*, Jan./Feb. 1989, 3 pages total.

Pinkham, "Inventor's CAD/CAM may transform dentistry," *Dentist*, Sep. 1990, 3 pages total.

Ponitz,"Invisible Retainers", *Am. J. Orthodontics*, vol. 59, No. 3, Mar. 1971, pp. 266-272.

Procera Research Projects, *PROCERA Research Projects 1993*—Abstract Collection, 1993, pp. 3-24.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow, "CAD/CAM in Dentistry: A Historical Perspective and View of the Future," *Journal*, vol. 58 No. 4, (Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasiblity of an Automated System for Production of Dental Restorations," PhD Thesis, Univ. of Minnesota, Nov. 1988, 244 pages total.

Richmond et al., Research Reports, "The Development of a 3D Cast Analysis System," *British Journal of Orthodontics*, vol. 13, No. 1, (Jan. 1986) pp. 53-54.

Richmond, "Recording The Dental Cast In Three Dimensions," *Am. J. Orthod. Dentofac. Orthop.*, vol. 92, No. 3, (Sep. 1987), pp. 199-206.

Rudge, "Dental arch analysis: arch form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Shilliday, "Minimizing finishing problems with the mini-positioner" *Am. J. Orthod.* 59:596-599, 1971.

Siemens, "CEREC—Computer-Reconstruction, "High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Dentistry" (Article Summary in English, article in German), *Dtsch Zahnärztl Z* 45, 314-322, 1990.

U.S. Department of Commerce, National Technical Information Service, "Automated Crown Replication Using Solid Photography SM," Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., "Three-Dimensional Analysis of Dental Casts by Means of the Optocom," *J Dent Res*, Jul-Aug. 1972, vol. 51, No. 4, p. 1100.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Várady et al., Reverse engineering of geometric models—an introduction. Computer-Aided Design, 29 (4):255-268, 1997.

Warunek et al., "Clinical use of silicone elastomer appliances" *JCO*, MH (10):694-700, 1989.

Warunek et al., "Physical And Mechanical Properties of Elastomers In Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution,"*Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing, " Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis Of Three-Dimensional Tooth Movement in Orthodontics," *Frontiers in Med. and Biol. Eng'g*, vol. 1, No. 2 (1988), pp. 119-130.

\* cited by examiner

SYSTEMS AND METHODS FOR REMOVING GINGIVA FROM COMPUTER TOOTH MODELS

CROSS-REFERENCES TO RELATED APPLICATIONS

This application is a continuation-in-part of application Ser. No. 09/640,328, filed Aug. 16, 2000 now U.S. Pat. No. 6,386,878. The full disclosure of the above application is incorporated herein by reference.

BACKGROUND OF THE INVENTION

1. Field of the Invention

The invention relates generally to the field of orthodontics and, more particularly, to computer-automated separation of a model of teeth.

2. Description of the Background Art

Tooth positioners for finishing orthodontic treatment are described by Kesling in the *Am. J. Orthod. Oral. Surg.* 31:297–304 (1945) and 32:285–293 (1946). The use of silicone positioners for the comprehensive orthodontic realignment of a patient's teeth is described in Warunek et al. (1989) *J. Clin. Orthod.* 23:694–700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) *J. Clin. Orthodon.* 30:673–680; Cureton (1996) *J. Clin. Orthodon.* 30:390–395; Chiappone (1980) *J. Clin. Orthodon.* 14:121–133; Shilliday (1971) *Am. J. Orthodontics* 59:596–599; Wells (1970) *Am. J. Orthodontics* 58:351–366; and Cottingham (1969) *Am. J. Orthodontics* 55:23–31.

Kuroda et al. (1996) *Am. J. Orthodontics* 110:365–369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

BRIEF SUMMARY OF THE INVENTION

In one aspect, a computer-implemented method separates a tooth from an adjacent structure, such as a gingiva, by defining a cutting surface; and applying the cutting surface between the tooth and the structure to separate the tooth in a single cut.

Implementations of the method may include one or more of the following. The cutting surface may be curved. The cutting surface may be expressed as a function, such as a spline function and a quadratic function. The quadratic function can be a parabolic function. The cutting surface can be interactively adjusted, wherein the interactive adjustment of the cutting surface modifies a function defining the cutting surface. The method can include interactively highlighting the separated portion and the border of the separated portion. The cutting surface can be defined by specifying a basis for the tooth. A gingival line separating a tooth surface and a gingiva can be determined. The method can include finding a high curvature location on the tooth surface. A spline can be fit to the gingival line. The cutting surface can be a plurality of surfaces. The root of the tooth can be modeled as a parabolic surface below a gingival line. The method can include defining an enclosing surface to enclose the crown of the tooth. The method also includes displaying the surface specified with a plurality of nodes; adjusting one or more nodes to modify the surface; and applying the surface to separate the gingiva from the tooth.

In another aspect, a system for separating a tooth from an adjacent structure, such as a gingiva, which includes means for defining a cutting surface; and means for applying the cutting surface between the tooth and the structure to separate the tooth from the structure in a single cut.

In another aspect, a computer program, residing on a tangible storage medium, for use in separating gingiva from a computer model of a tooth, the program comprising executable instructions operable to cause a computer to: define a cutting surface along the gingiva; and apply the cutting surface to the tooth to separate the gingiva from the tooth in a single cut.

In another aspect, a computer program, residing on a tangible storage medium, for use in a computer model of a tooth from a computer model of a dental structure, the program comprising executable instructions operable to cause a computer to: define a cutting surface, wherein the cutting surface is expressed as a spline function and a quadratic function; and apply the cutting surface between the computer model of the dental structure and the computer model of the tooth to separate the computer models in a single cut.

In yet another aspect, a computer has a processor, a data storage device coupled to the processor, the data storage device containing code for use in separating a computer model of a tooth from a computer model of an adjacent structure, the program comprising executable instructions operable to cause a computer to: define a cutting surface, wherein the cutting surface is expressed as a spline function and a quadratic function and wherein the cutting surface further comprises a plurality of surfaces and wherein the root of the tooth is modeled as a parabolic surface below a gingival line; and apply the cutting surface to the tooth to separate the gingiva from the tooth in a single cut.

In yet another aspect, a computer-implemented method for separating a dental structure from an adjacent tooth which includes defining a cutting surface along the gingiva; and applying the cutting surface to the tooth to separate the gingiva and reconstruct the root for the tooth in a single cut.

Advantages of the system may include one or more of the following. The system provides a flexible cutter that can be modified to follow the gingival line so user could cut off the gingiva in one single cut. The gingival line defined by user here could also be reused later for the gingival reconstruction process.

Advantages of the invention may include one or more of the following. The system separates gingiva from tooth in a single cut. The system also reconstructs the tooth to provide a root for the tooth in the same operation. The system also generates a crown surface portion of a tooth model relatively quickly by applying the computed functions. The speed in drawing the crown surface allows real time shaping by the user when the user moves the crown control points and the top control points or when the user edits the gingival line. Also it facilitates the finding of the intersection as the system can rapidly determine whether a given point, such as a vertex of the tooth mesh, is inside or outside the gingival cutting surface.

DETAILED DESCRIPTION OF THE INVENTION

Figure 1A:
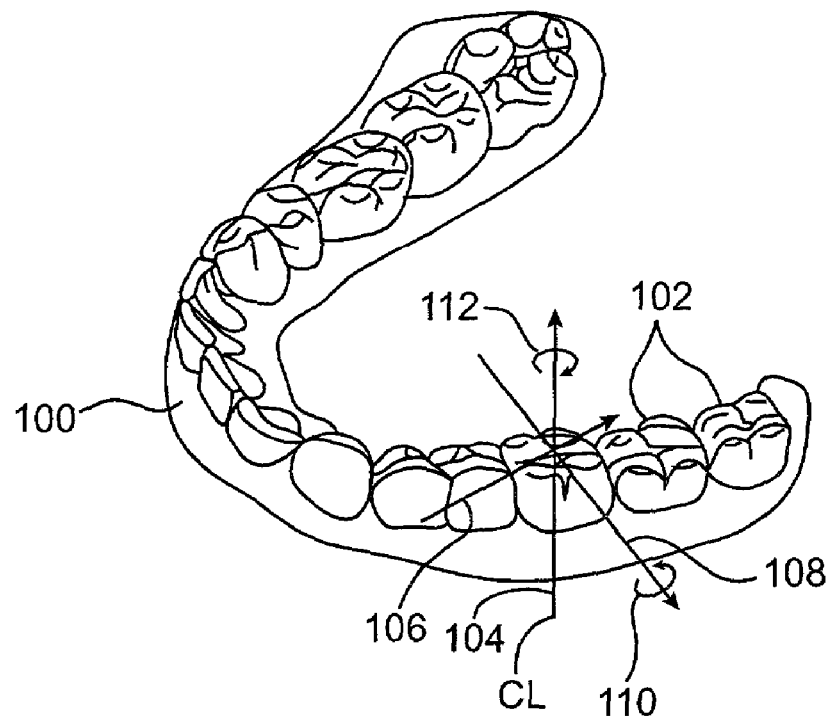
FIG. 1A illustrates a patient's jaw and provides a general indication of how teeth may be moved.

Referring now to FIG. 1A, a representative jaw 100 includes sixteen teeth, at least some of which are to be moved from an initial tooth arrangement to a final tooth arrangement. To understand how the teeth may be moved, an arbitrary centerline (CL) is drawn through one of the teeth 102. With reference to this centerline (CL), the teeth may be moved in the orthogonal directions represented by axes 104, 106, and 108 (where 104 is the centerline). The centerline may be rotated about the axis 108 (root angulation) and 104 (torque) as indicated by arrows 110 and 112, respectively. Additionally, the tooth may be rotated about the centerline. Thus, all possible free-form motions of the tooth can be performed.

Figure 1B:
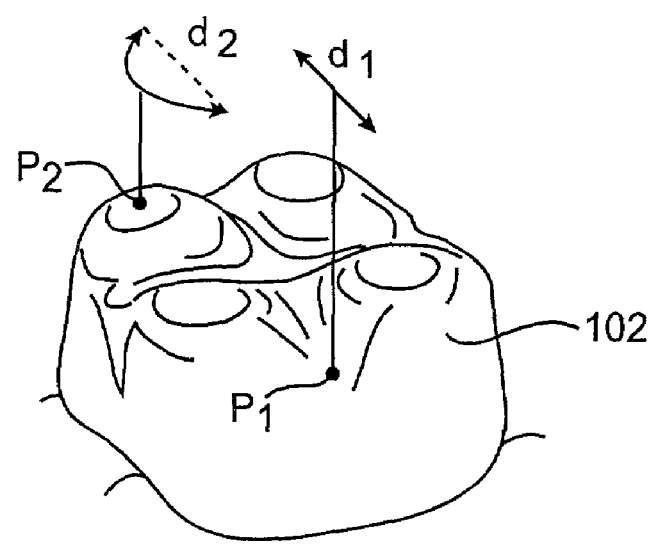
FIG. 1B illustrates a single tooth from FIG. 1A and defines how tooth movement distances are determined.

Referring now to FIG. 1B, the magnitude of any tooth movement is defined in terms of the maximum linear translation of any point P on a tooth 102. Each point $P_i$ will undergo a cumulative translation as that tooth is moved in any of the orthogonal or rotational directions defined in FIG. 1A. That is, while the point will usually follow a non-linear path, there will be a linear distance between any point in the tooth when determined at any two times during the treatment. Thus, an arbitrary point $P_1$ may in fact undergo a true side-to-side translation as indicated by arrow $d_1$, while a second arbitrary point $P_2$ may travel along an arcuate path, resulting in a final translation $d_2$. In many situations, the maximum permissible movement of a point $P_i$ in any particular tooth is defined as the maximum linear translation of that point $P_i$ on the tooth that undergoes the maximum movement for that tooth in any treatment step.

One tool for incrementally repositioning the teeth is a set of one or more adjustment appliances. Suitable appliances include any of the known positioners, retainers, or other removable appliances that are used for finishing and maintaining teeth positions in connection with conventional orthodontic treatment. As described below, a plurality of such appliances can be worn by a patient successively to achieve gradual tooth repositioning. A particularly advantageous appliance is the appliance 111, shown in FIG. 1C, which typically comprises a polymeric shell having a cavity shaped to receive and resiliently reposition teeth from one tooth arrangement to another tooth arrangement. The polymeric shell typically fits over all teeth present in the upper or lower jaw. Often, only some of the teeth will be repositioned while others will provide a base or anchor region for holding the repositioning appliance in place as it applies the resilient repositioning force against the tooth or teeth to be repositioned. In complex cases, however, many or most of the teeth will be repositioned at some point during the treatment. In such cases, the teeth that are moved can also serve as a base or anchor region for holding the repositioning appliance. The gums and the palette also serve as an anchor region in some cases, thus allowing all or nearly all of the teeth to be repositioned simultaneously.

Figure 1C:
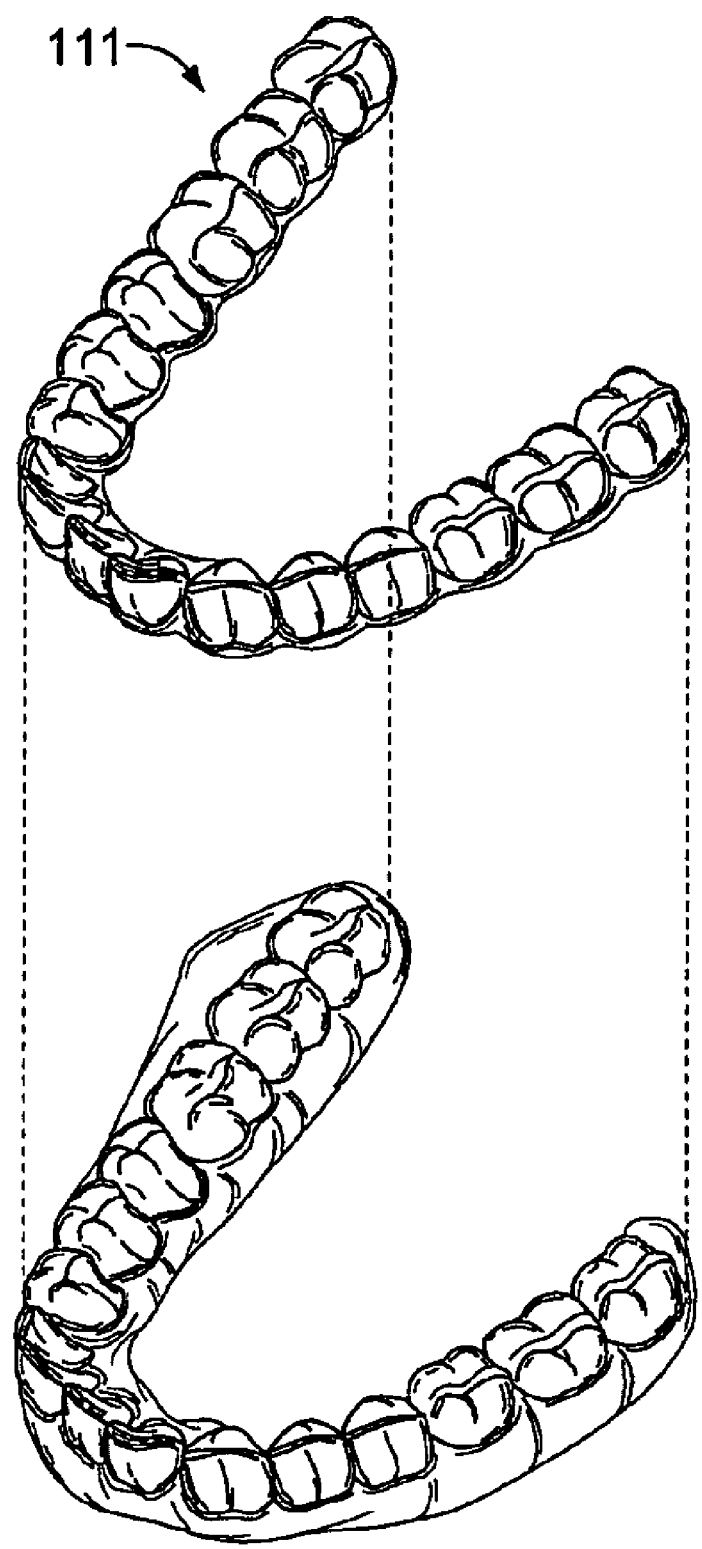
FIG. 1C illustrates the jaw of FIG. 1A together with an incremental position adjustment appliance.

The polymeric appliance 111 of FIG. 1C is preferably formed from a thin sheet of a suitable elastomeric polymeric, such as Tru-Tain 0.03 in. thermal forming dental material, marketed by Tru-Tain Plastics, Rochester, Minn. 55902. In many cases, no wires or other means are provided for holding the appliance in place over the teeth. In some cases, however, it is necessary to provide individual attachments on the teeth with corresponding receptacles or apertures in the appliance 111 so that the appliance can apply forces that would not be possible or would be difficult to apply in the absence of such attachments.

Figure 2:
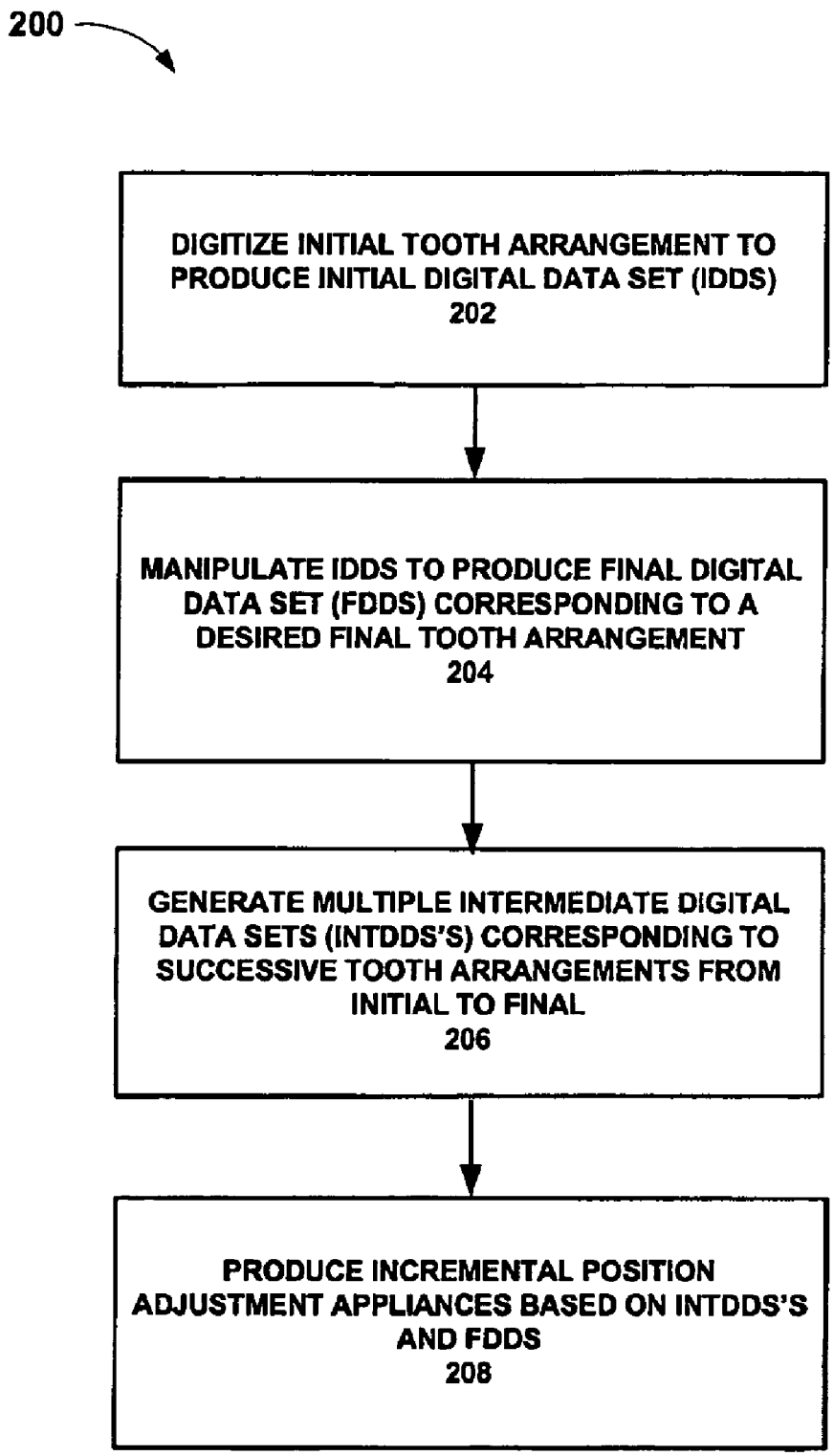
FIG. 2 is a block diagram illustrating steps for producing a system of incremental position adjustment appliances.

FIG. 2 shows a process 200 for producing the incremental position adjustment appliances for subsequent use by a patient to reposition the patient's teeth. As a first step, an initial digital data set (IDDS) representing an initial tooth arrangement is obtained (step 202). The IDDS may be obtained in a variety of ways. For example, the patient's teeth may be scanned or imaged using X-rays, three dimensional X-rays, computer-aided tomographic images or data sets, or magnetic resonance images, among others. More details on the contact or non-contact scanners are in commonly-owned and co-pending application Ser. No. 09/169,276, filed Oct. 8, 1998, the content of which is incorporated by reference.

A plaster cast of the patient's teeth is obtained by well known techniques, such as those described in Graber, Orthodontics: Principle and Practice, Second Edition, Saunders, Pa., 1969, pp. 401–415. After the tooth casting is obtained, the casting is digitally scanned by a scanner, such as a non-contact type laser or destructive scanner or a contact-type scanner, to produce the IDDS. The data set produced by the scanner may be presented in any of a variety of digital formats to ensure compatibility with the software used to manipulate images represented by the data. In addition to the 3D image data gathered by laser scanning or destructive scanning the exposed surfaces of the teeth, a user may wish to gather data about hidden features, such as the roots of the patient's teeth and the patient's jaw bones. This information is used to build a detailed model of the patient's dentition and to show with more accuracy and precision how the teeth will respond to treatment. For example, information about the roots allows modeling of all tooth surfaces, instead of just the crowns, which in turn allows simulation of the relationships between the crowns and the roots as they move during treatment. Information about the patient's jaws and gums also enables a more accurate model of tooth movement during treatment. For example, an x-ray of the patient's jaw bones can assist in identifying any close teeth, and an MRI can provide information about the density of the patient's gum tissue. Moreover, information about the relationship between the patient's teeth and other cranial features allows accurate alignment of the teeth with respect to the rest of the head at each of the treatment steps. Data about these hidden features may be gathered from many sources, including 2D and 3D x-ray systems, CT scanners, and magnetic resonance imaging (MRI) systems. Using this data to introduce visually hidden features to the tooth model is described in more detail below.

The IDDS is manipulated using a computer having a suitable graphical user interface (GUI) and software appropriate for viewing and modifying the images. More specific aspects of this process will be described in detail below.

Individual tooth and other components may be segmented or isolated in the model to permit their individual repositioning or removal from the digital model. After segmenting or isolating the components, the user will often reposition the tooth in the model by following a prescription or other written specification provided by the treating professional. Alternatively, the user may reposition one or more teeth based on a visual appearance or based on rules and algorithms programmed into the computer. Once the user is satisfied, the final teeth arrangement is incorporated into a final digital data set (FDDS) (step 204).

The FDDS is used to generate appliances that move the teeth in a specified sequence. First, the centers of each tooth model may be aligned using a number of methods. One method is a standard arch. Then, the teeth models are rotated until their roots are in the proper vertical position. Next, the teeth models are rotated around their vertical axis into the proper orientation. The teeth models are then observed from the side, and translated vertically into their proper vertical position. Finally, the two arches are placed together, and the teeth models moved slightly to ensure that the upper and lower arches properly mesh together. The meshing of the upper and lower arches together is visualized using a collision detection process to highlight the contacting points of the teeth.

In step 204, final positions for the upper and lower teeth in a masticatory system of a patient are determined by generating a computer representation of the masticatory system. An occlusion of the upper and lower teeth is computed from the computer representation; and a functional occlusion is computed based on interactions in the computer representation of the masticatory system. The occlusion may be determined by generating a set of ideal models of the teeth. Each ideal model in the set of ideal models is an abstract model of idealized teeth placement, which is customized to the patient's teeth, as discussed below. After applying the ideal model to the computer representation, the position of the teeth is optimized to fit the ideal model. The ideal model may be specified by one or more arch forms, or may be specified using various features associated with the teeth.

Based on both the IDDS and the FDDS, a plurality of intermediate digital data sets (INTDDSs) are defined to correspond to incrementally adjusted appliances (step 206). Finally, a set of incremental position adjustment appliances are produced based on the INTDDs and the FDDS (step 208).

Figure 3:
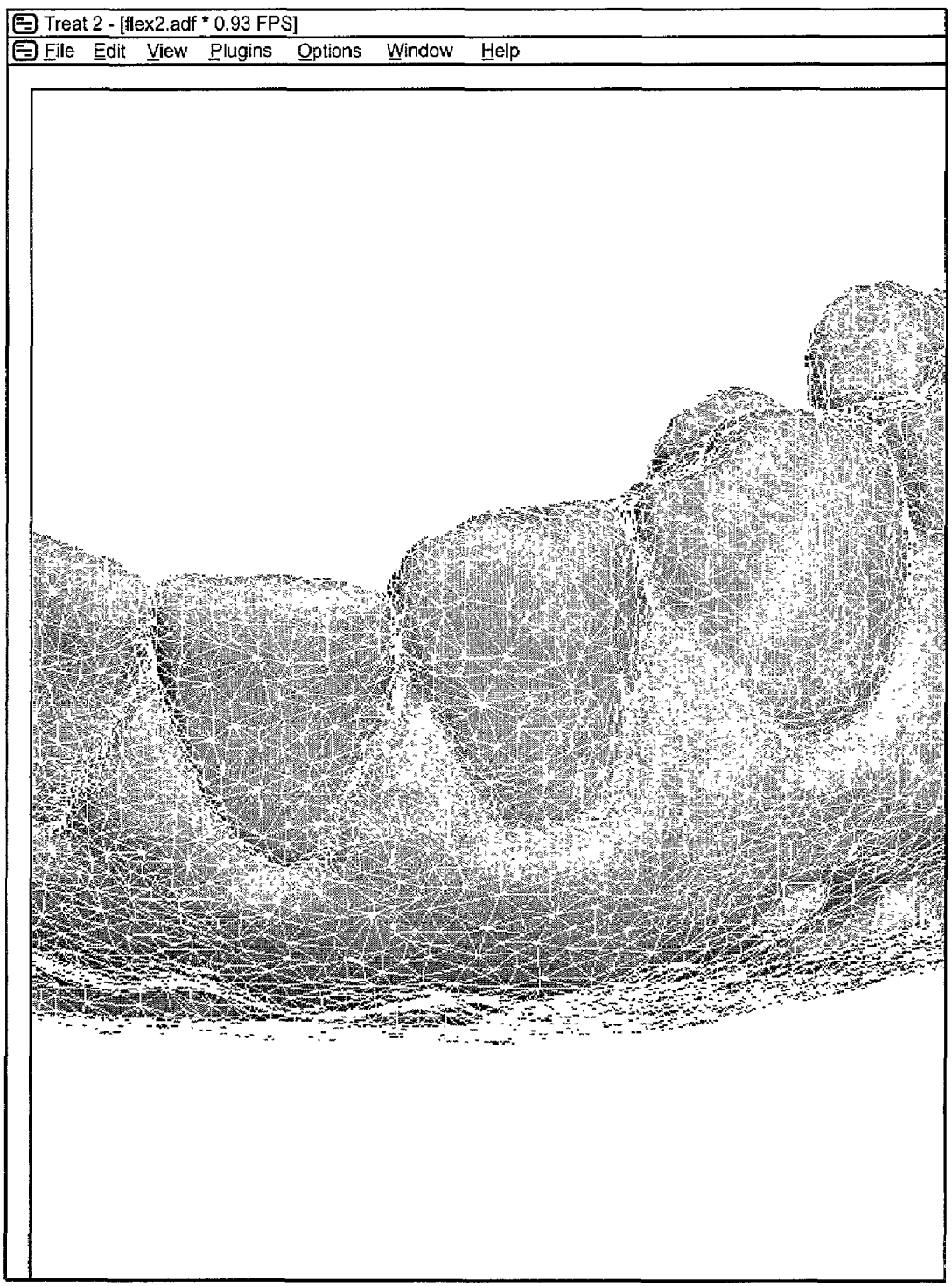
FIG. 3 is an illustration of a 3D model of teeth using triangular meshes.
Figure 3:
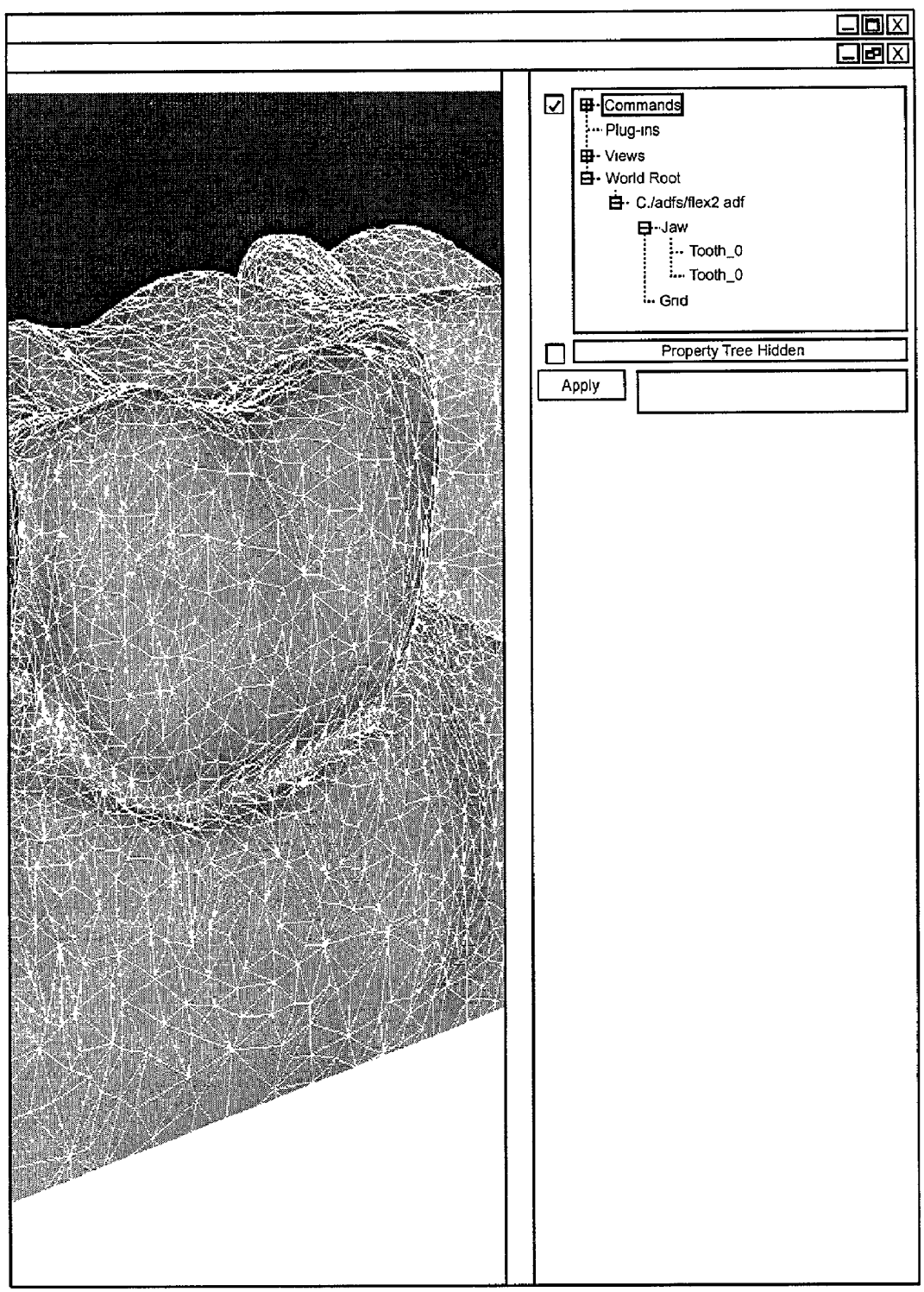

FIG. 3 shows one exemplary 3D surface model of the teeth. The surface topology of a 3D model of teeth on a jaw can be modeled as a set of polygons of appropriate sizes and shapes joined at their edges. The set of polygons defining the 3D object is referred to as the "model" or "mesh" for the 3D object. In one embodiment, the polygons are triangles. In this embodiment, a triangle mesh is a piecewise linear surface with triangular faces joined along their edges.

Many types of scan data, such as that acquired by an optical scanning system, provide a 3D geometric model (e.g., a triangular surface mesh) of the teeth when acquired. Other scanning techniques, such as the destructive scanning technique described above, provide data in the form of volume elements ("voxels") that can be converted into a digital geometric model of the tooth surfaces. In one implementation, a marching cubes algorithm is applied to convert the voxels into a mesh, which can undergo a smoothing operation to reduce the jaggedness on the surfaces of the tooth model caused by the marching cubes conversion. One smoothing operation moves individual triangle vertices to positions representing the averages of connected neighborhood vertices to reduce the angles between triangles in the mesh.

Another optional step is the application of a decimation operation to the smoothed mesh to eliminate data points, which improves processing speed. After the smoothing and decimation operation have been performed, an error value is calculated based on the differences between the resulting mesh and the original mesh or the original data, and the error is compared to an acceptable threshold value. The smoothing and decimation operations are applied to the mesh once again if the error does not exceed the acceptable value. The last set of mesh data that satisfies the threshold is stored as the tooth model.

The triangles in FIG. 3 form a connected graph. In this context, two nodes in a graph are connected if there is a sequence of edges that forms a path from one node to the other (ignoring the direction of the edges). Thus defined, connectivity is an equivalence relation on a graph: if triangle A is connected to triangle B and triangle B is connected to triangle C, then triangle A is connected to triangle C. A set of connected nodes is then called a patch. A graph is fully connected if it consists of a single patch. The processes discussed below keep the triangles connected.

The mesh model can also be simplified by removing unwanted or unnecessary sections of the model to increase data processing speed and enhance the visual display. Unnecessary sections include those not needed for creation of the tooth repositioning appliance. The removal of these unwanted sections reduces the complexity and size of the digital data set, thus accelerating manipulations of the data set and other operations. After the user positions and sizes the eraser tool and instructs the software to erase the unwanted section, all triangles within the box set by the user are removed and the border triangles are modified to leave a smooth, linear border. The software deletes all of the triangles within the box and clips all triangles that cross the border of the box. This requires generating new vertices on the border of the box. The holes created in the model at the faces of the box are retriangulated and closed using the newly created vertices.

In alternative embodiments, the computer automatically simplifies the digital model by performing the user-oriented functions described above. The computer applies knowledge of orthodontic relevance to determine which portions of the digital model are unnecessary for image manipulation.

Once a 3D model of the tooth surfaces has been constructed, models of the patient's individual teeth can be derived. In one approach, individual teeth and other components are "cut" using a cutting tool to permit individual repositioning or removal of teeth in or from the digital data. After the components are "freed," a prescription or other written specification provided by the treating professional is followed to reposition the teeth. Alternatively, the teeth may be repositioned based on the visual appearance or based on rules and algorithms programmed into the computer. Once an acceptable final arrangement has been created, the final tooth arrangement is incorporated into a final digital data set (FDDS).

Figure 4:
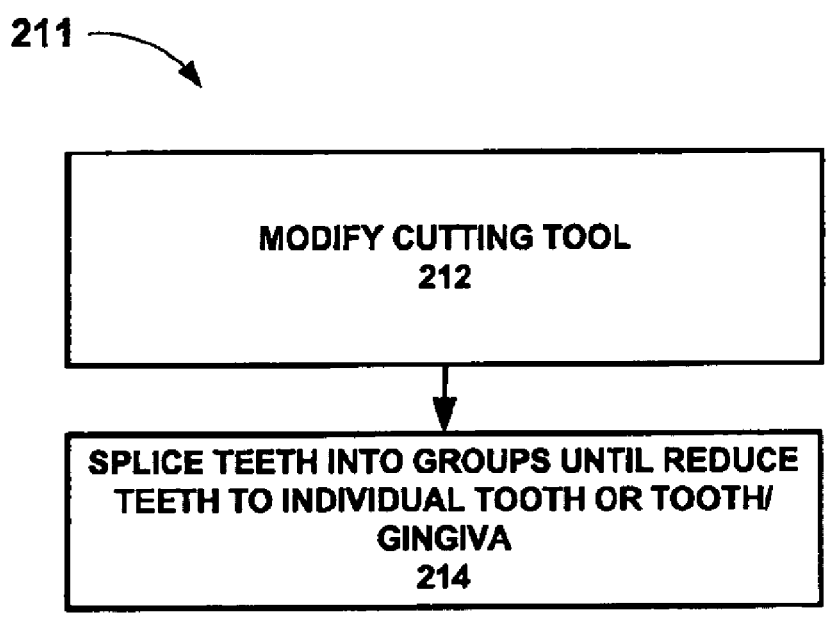
FIG. 4 is a flow chart illustrating a process for repetitively separating a group of teeth into two groups of teeth.

Referring now to FIG. 4, a process 211 for separating all teeth into individual units is shown. First, the process 211 customizes a cutting tool (step 212). Next, using the cutting tool, the user or an automated process applies the cutting tool to repetitively break up the group of teeth into two smaller groups until the teeth have been reduced into an individual unit (step 214). A viewer program displays an initial image of the teeth and, if requested by the user, an image of the separated teeth. The user can rotate the images in three dimensions to view the various tooth surfaces, and the clinician can snap the image to any of several predefined viewing angles. These viewing angles include the standard front, back, top, bottom and side views, as well as orthodontic-specific viewing angles, such as the lingual, buccal, facial, occlusal, and incisal views.

A saw tool is used to define the individual teeth (or possibly groups of teeth) to be moved. The tool separates the scanned image into individual geometric components enabling the software to move the tooth or other component images independent of remaining portions of the model. In one embodiment, the saw tool defines a path for cutting the graphic image by using two cubic B-spline curves lying in space, possibly constrained to parallel planes, either open or closed. A set of lines connects the two curves and shows the user the general cutting path. The user may edit the control points on the cubic B-splines, the thickness of the saw cut, and the number of erasers used, as described below.

In an alternative embodiment, the teeth are separated by using the saw as a "coring" device, cutting the tooth from above with vertical saw cuts. The crown of the tooth, as well as the gingivae tissue immediately below the crown are separated from the rest of the geometry, and treated as an individual unit, referred to as a tooth. When this model is moved, the gingivae tissue moves relative to the crown, creating a first order approximation of the way that the gingivae will reform within a patient's mouth.

Each tooth may also be separated from the original trimmed model. Additionally, a base may be created from the original trimmed model by cutting off the crowns of the teeth. The resulting model is used as a base for moving the teeth. This facilitates the eventual manufacture of a physical mold from the geometric model, as described below.

Thickness: When a cut is used to separate a tooth, the user will usually want the cut to be as thin as possible. However, the user may want to make a thicker cut, for example, when shaving down surrounding teeth, as described above. Graphically, the cut appears as a curve bounded by the thickness of the cut on one side of the curve.

Number of Erasers: A cut is comprised of multiple eraser boxes arranged next to each other as a piecewise linear approximation of the Saw Tool's curve path. The user chooses the number of erasers, which determines the sophistication of the curve created: the greater the number of segments, the more accurately the cutting will follow the curve. The number of erasers is shown graphically by the number of parallel lines connecting the two cubic B-spline curves. Once a saw cut has been completely specified the user applies the cut to the model. The cut is performed as a sequence of erasings, with a single erasing iteration of the cut as described in the algorithm for a open ended B-spline curve. For a vertical cut, the curves are closed, with $P_A$ [O] and $P_A$ [S] being the same point and $P_B$ [O] and $P_B$ [S] being the same point.

In one embodiment, the software automatically partitions the saw tool into a set of erasers based upon a smoothness measure input by the user. The saw is adaptively subdivided until an error metric measures the deviation from the ideal representation to the approximate representation to be less than a threshold specified by the smoothness setting. One error metric compares the linear length of the subdivided curve to the arclength of the ideal spline curve. When the difference is greater than a threshold computed from the smoothness setting, a subdivision point is added along the spline curve.

A preview feature may also be provided in the software. The preview feature visually displays a saw cut as the two surfaces that represent opposed sides of the cut. This allows the user to consider the final cut before applying it to the model data set.

In one embodiment, a flexible plane can be used to splice two more teeth into two groups of teeth. The process displays one or more teeth for the user to review and displays a flexible plane with a plurality of control grid nodes. The flexible plane is formed by a number of surface patches called bicubic Bézier patches. The equation of such patch is well known, and it can be described as:

$$S(u, v) = \sum_{i=0}^{3} \sum_{k=0}^{3} b_{i,k} B_k^m(u) B_i^n(v)$$

where u, and v are coordinates in 3D space chosen along a straight plane between the two teeth, and S is the function along the ortho-normal direction to the straight plane, $b_{i,k}$ represents a Bézier point of the patch, and $B_i^n(t) = {}_nC_t(1-t)^{n-i} t^i, i = 0, 1, \ldots, n$ denotes the Bernstein polynomials.

The process accepts user adjustments to the position of various grid nodes to modify the flexible plane. The cutting curve and tooth portions associated with a flexible plane are then updated in real time. The user can repetitively perform these operations to separate all teeth into individual tooth that is ready for manipulation.

Figure 5:
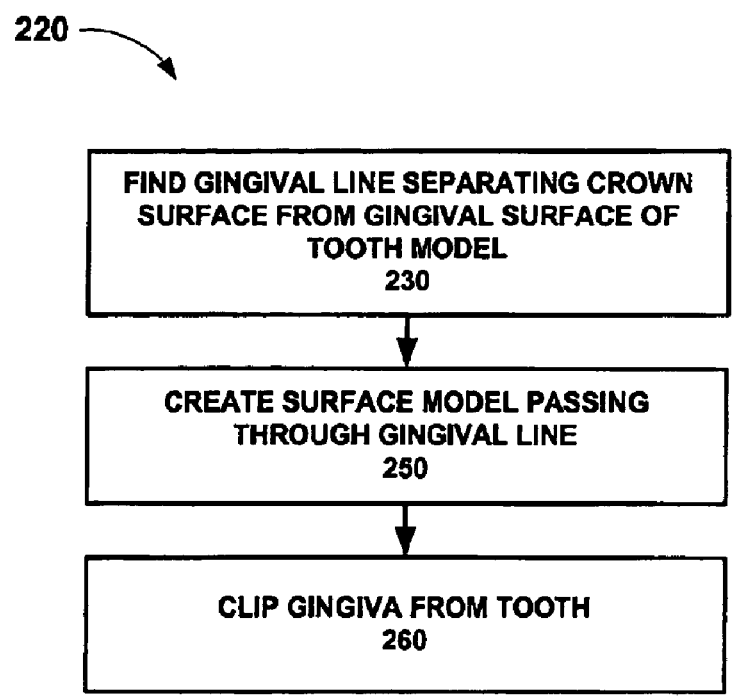
FIG. 5 is a flow chart illustrating a process for cutting or splicing gingiva from a tooth model.

FIG. 5 shows a process 220 to cut or splice gingiva from a tooth model. Initially, a user selects a tooth to be cut. The process 220 then determines whether a gingival line can be located, and if so, a cutter is applied to follow this gingival line. Referring now to FIG. 5, the gingival line is the line that separates the clinical crown surface of the tooth from the gingival surface in the computer model of the tooth (step 230). Next, the process 220 creates a closed surface model of a cutting line that passes through the above found gingival line (step 250). The surface should not cut through the clinical crown portion and should create an approximate root shape. The cutting line is part of a closed surface model that passes exactly through the gingival line of the tooth.

Next, the process 220 clips the gingiva from the tooth using a curved clipping algorithm (260) as described in U.S. patent application Ser. No. 09/539,185, filed on Mar. 30, 2000, entitled "System for Separating Teeth Model"; and U.S. patent application Ser. No. 09/539,021, filed on Mar. 30, 2000, entitled "Flexible Plane for Separating Teeth Model," the contents of which are incorporated by reference.

The process 220 cuts out the gingival portion of the tooth that has been already separated in a single cut operation and at the same time reconstructs a relatively close root shape.

Figure 6:
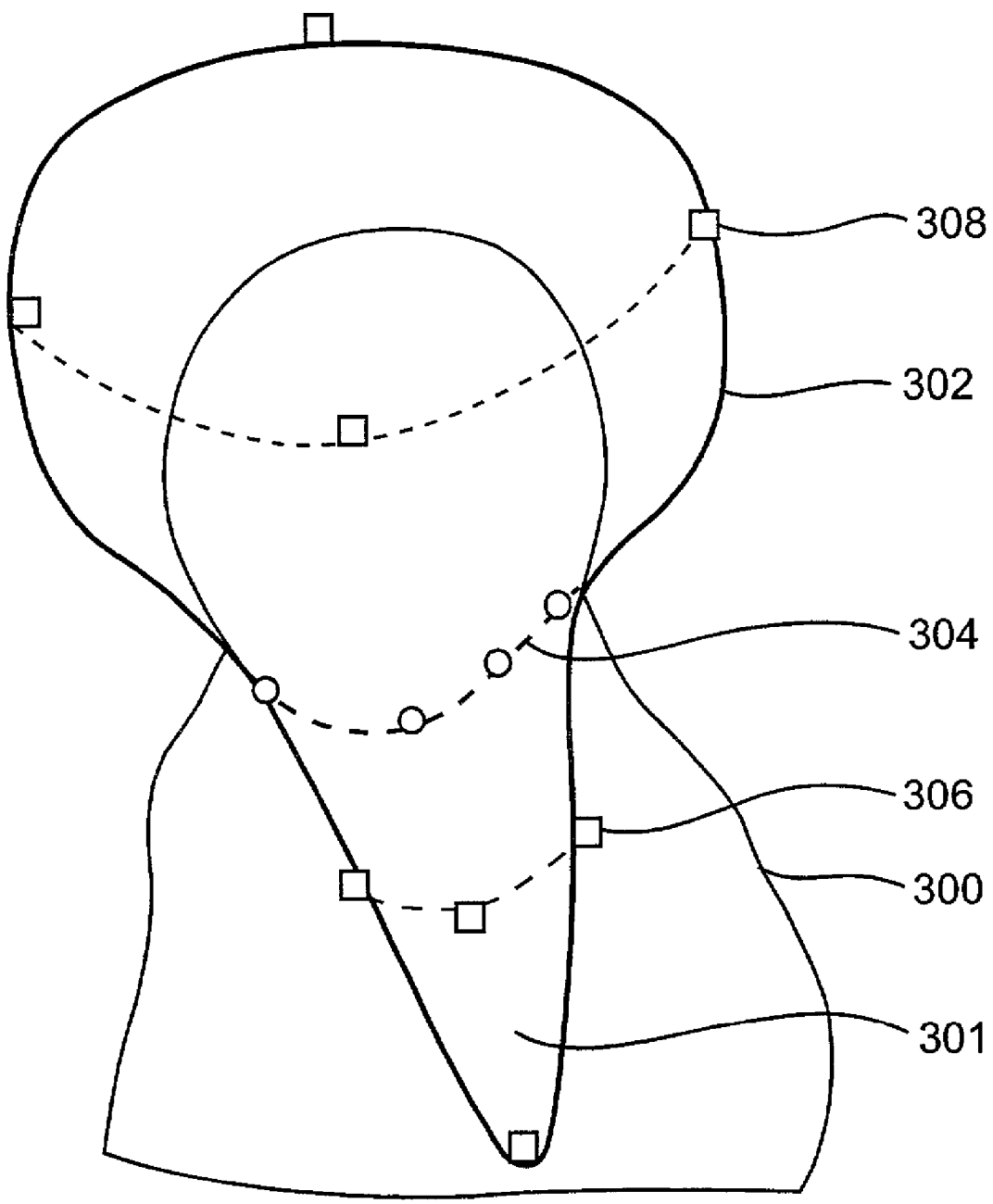
FIG. 6 shows an exemplary cone shaped cutter and control points for the cutter.

The cutter of FIG. 5 embeds itself into the tooth to be cut. In the embodiment of FIG. 6, the cutter is shaped like an ice-cream cone, with the top surrounding the crown of a tooth 301 to be extracted, and the bottom embedded inside the gingiva 300 to define the root of the tooth 301. The gingival line or curve defines a rim 304 for this ice-cream cone shaped cutter. The cutter is shaped by several sets of control points. The points on the rim 304 (gingival curve) controls give the definition of the gingival line. This set of control points can be moved on the surface of the tooth 301. One or more crown control points 308 define the upper part of the cutter. This set of crown control points 308 can be adjusted to enclose the crown part of the tooth by the upper part of the cutter. The crown control points 308 are also adjusted also so that the crown part of the gingival cutter does not cut through any gingiva 300.

Additionally, root control points 306 are provided. The behavior of these control points differs than crown controls points 308 in that the set of control points 306 can only be moved in one direction, in and out, except for the pivot control point that can also be moved up and down, and by doing so would actually move all the root controls up and down with it. The goal of adjusting the set of root control points 306 is to define a starting root structure for the cutting tooth.

The system also provides one top control that defines the height of the upper part and one bottom control that defines the depth of the root part. Both can be moved in the up and down direction. The purpose of adjusting the top control point is so that all the crown part of tooth is enclosed within the cutter whereas the purpose of adjusting the bottom control point is to set proper root depth. Additionally, the gingival line can be visualized in a distinguishing color and can be drawn with more emphasis than other lines to enable better visualization during the editing of the gingival cut. The gingival curve created during this process can also be reused in gingival reconstruction. More details on gingival reconstruction can be found in co-pending application having Ser. No. 09/311,716 entitled "Digitally Modeling the Deformation of Gingival Tissue During Orthodontic Treatment," filed May 14, 1999, the content of which is hereby incorporated by reference.

Figure 7:
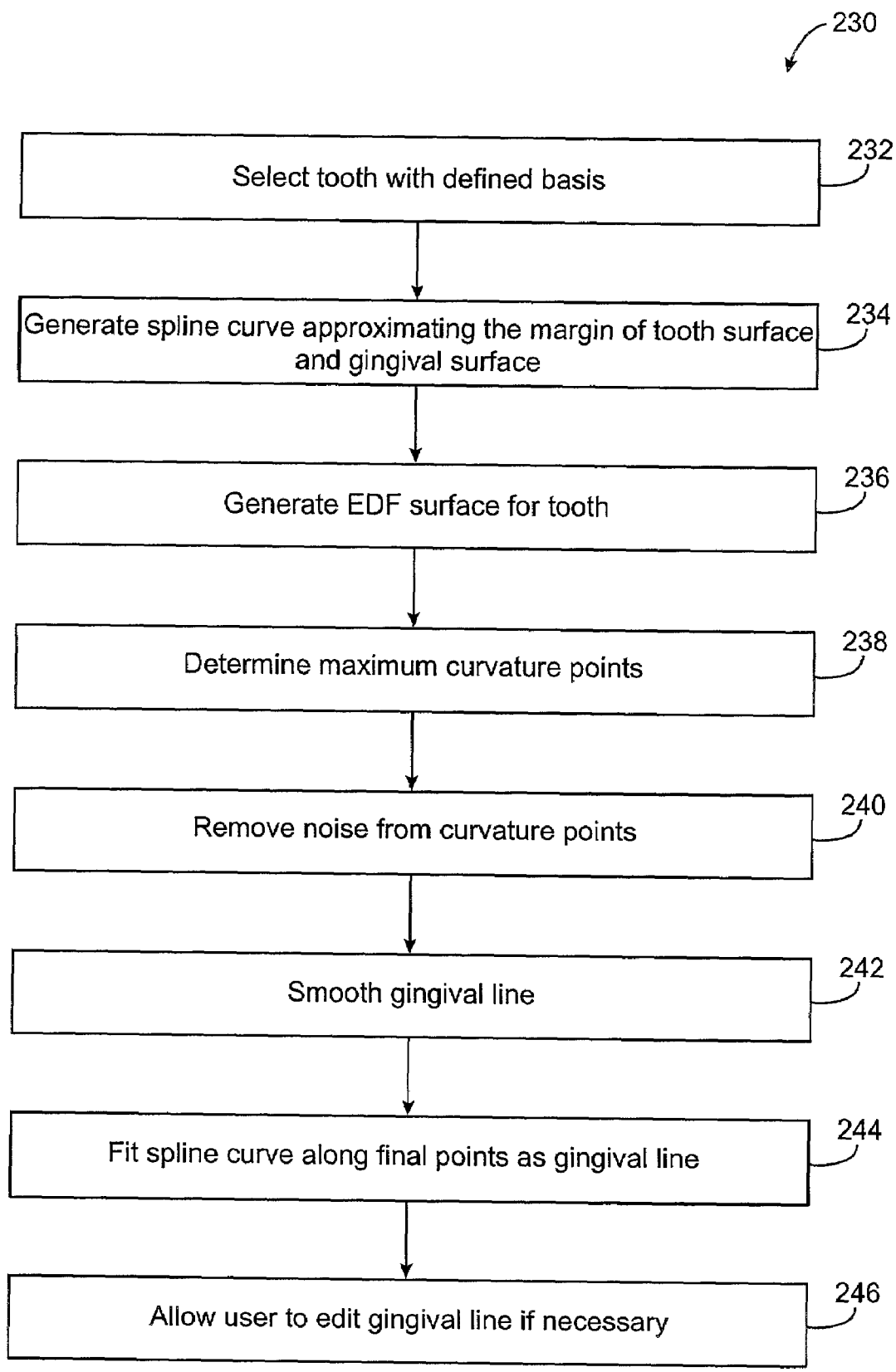
FIG. 7 is a flow chart illustrating the automatic finding of a gingival line.

FIG. 7 shows step 230 of FIG. 5 in more detail. The process of FIG. 7 performs automatic finding of a gingival line. First, the user selects a tooth that has a properly defined basis (step 232) and identification number. For example, the z-axis traverses along the top of the tooth, center is set at an approximate center of the tooth, and the y-axis starts from a lingual to labial surface. The tooth basis thus defined is also used in other parts of the treatment process. The process of FIG. 7generates a spline-curve that approximates the margin of tooth surface and gingival surface in the computer model of the tooth (step 234). The process of FIG. 7 then generates an EDF surface for the given tooth (step 236).

Next, along a preset number of angles around the z-axis of the tooth, the maximum curvature points along z-direction are found (step 238). These curvature points are found only in the area where a given tooth type could have gingival line. This eliminates finding numerous high curvature points, which are elsewhere due to noise and tooth features themselves. A filtering procedure is used to filter out the points generated by noise in the data (step 240). As the gingival line is often not quite smooth, a smoothing procedure is applied to adjust certain points and to eliminate noisy points on the curve (step 242). A smooth spline curve is fit along the final set of points that are available after filtering and smoothing procedure (step 244). This spline curve represents the gingival line for this tooth. The spline curve can optionally be edited by moving one or more control points on this curve (step 246).

Figure 8A:
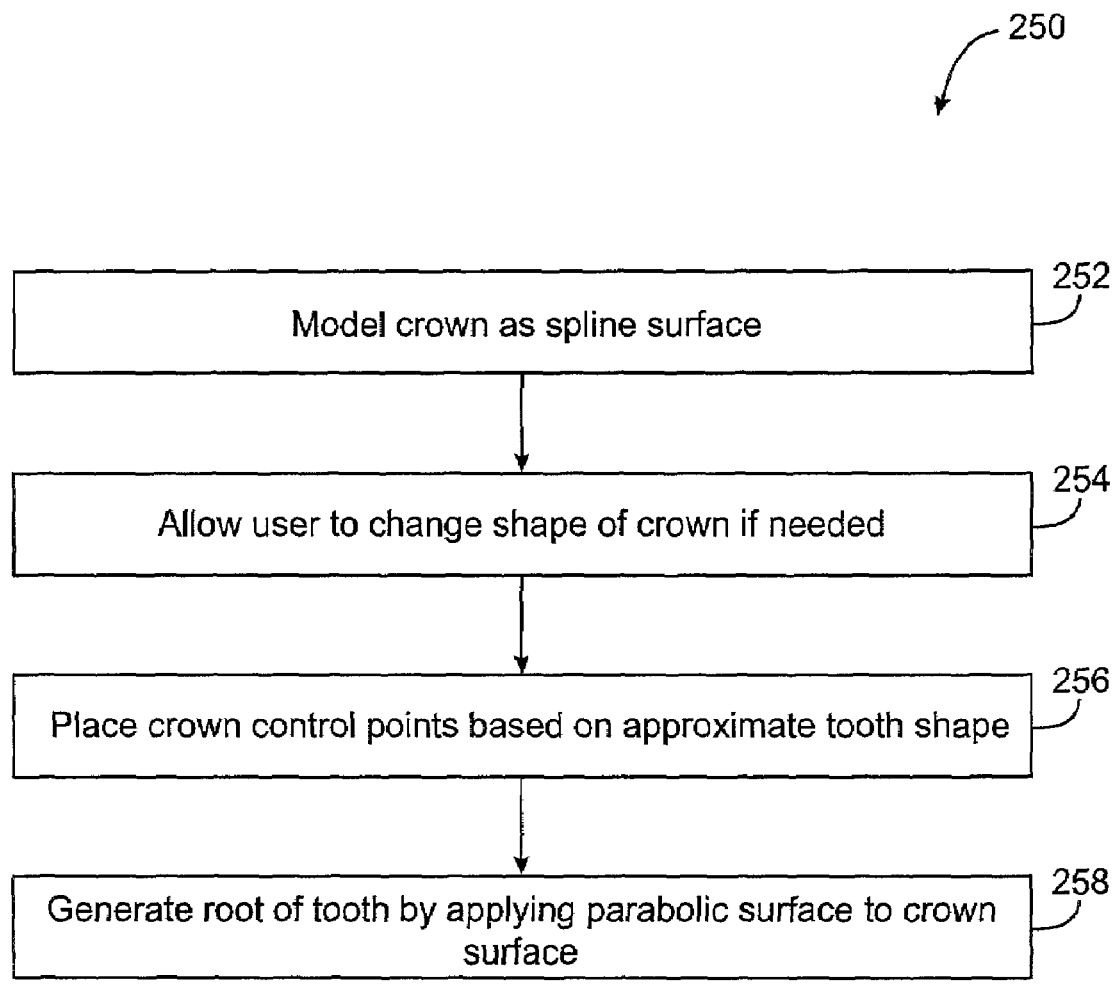
FIG. 8A is a flow chart illustrating creation of a surface model with a cut gingiva.

FIG. 8A shows in more detail a process for step 250 of FIG. 5 to create a surface model with a cut gingiva. The input for this process is the gingival line found in the steps above, the bounding box of the tooth, and a universal tooth identification that specifies the type of tooth it is. The process generates a closed surface model that passes through the gingival line. The surface has three distinct surfaces: a) a crown surface which starts at the gingival line and encloses all of the clinical crown part of the tooth; b) a parabolic surface that is inside the gingiva approximately at the bottom part of the root of the tooth; and c) a curved surface that connects the parabolic root bottom to the crown surface. In one embodiment, the surface pieces are modeled in cylindrical coordinate system (r, theta, Z).

The process of FIG. 8A models the crown surface as a spline surface which passes through the gingival line and a set of points (crown control points) around the clinical crown portion of the tooth, and a point above the top of the crown (step 252). First at a predetermined angles (phi) around z axis, the gingival curve is intersected with the half plane starting at z-axis at angle phi. Another point is computed depending up on the tooth type, a bit away from the tooth surface and above the gingival line. Quadratic curves are constructed at each angle from top control point to the gingival point and passing through the crown control point. Next, through all the points thus found for crown controls, a spline is fit around the z-axis. Thus the crown surface is defined by generating a grid of points that are quadratic along x-axis and cubic around z-axis. The crown control points can be edited to change the shape of the crown portion of the surface (step 254). For example, the point above the top of the tooth can be moved in the z-direction to change the shape of the crown surface portion.

Figure 8B:
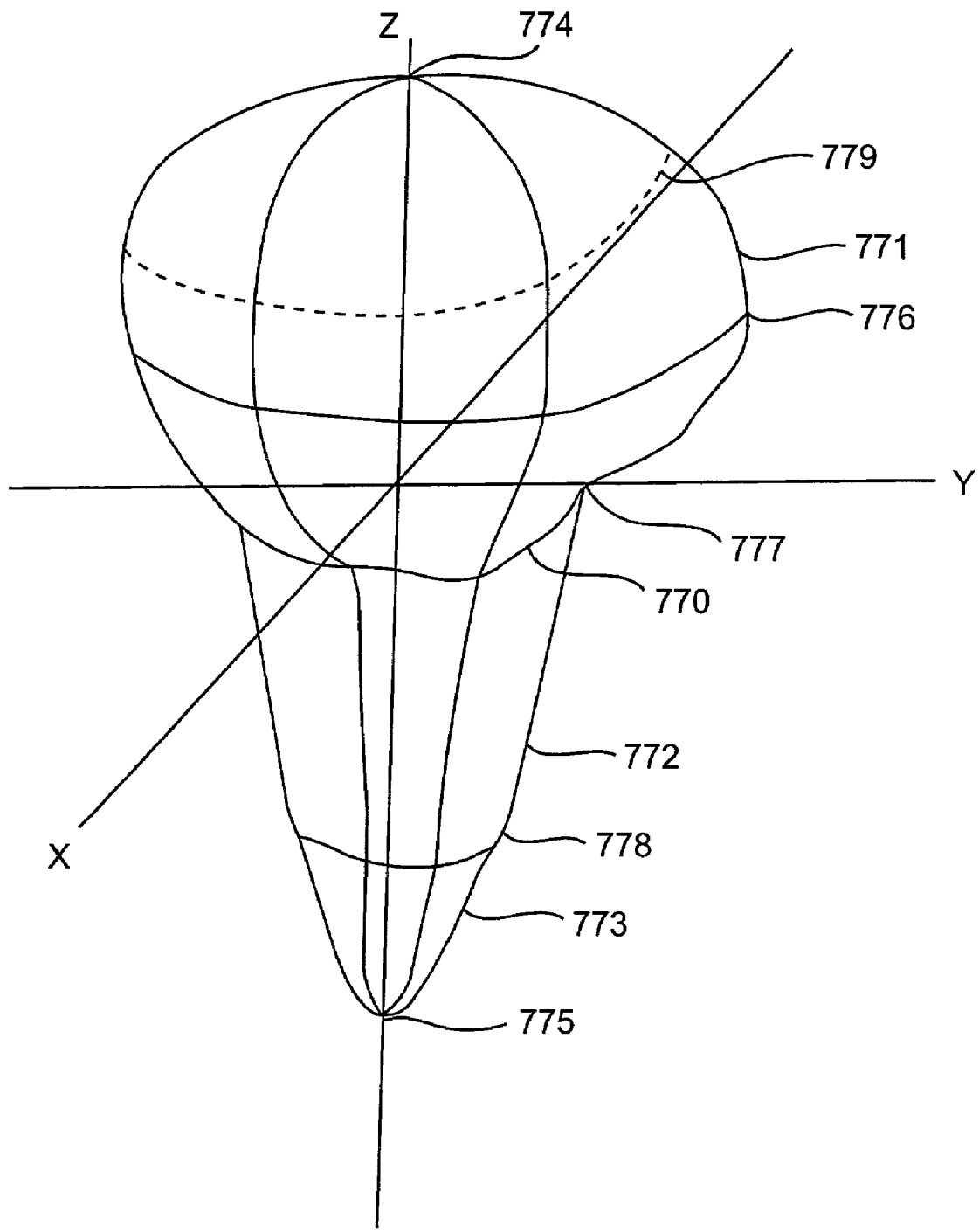
FIG. 8B shows an exemplary surface model with a cut gingiva.

FIG. 8B shows a description of the construction of the cutter surface. This figure shows four meridians of the surface around z-axis. The portion of each meridian that is above the gingival line is called a crown portion 771. This is modeled as a quadratic function in polar coordinates. In one embodiment, the mathematical representation of the curve is, $$a*\sqrt{z}+b*z=r$$

where "a" and "b" are constants. The function can be used to find radius of the point that is equidistant from z-axis for any given z value. The constants a and b are determined by the points through which the curve is passing, namely, a top point 774, a crown point 776 and the gingival point 777.

The portion of the meridian curve that lies below the gingival line 770 has two curves 772 and 773. The curve 772 is linear from the gingival point 777 to a root control point 778. The curve 773 is parabolic with vertex at a bottom control point 775. In one embodiment, this curve is represented by the function $$r=d\_a*(z-d\_b)**2+d\_c$$

where d_a, d_b and d_c are constants and can be computed from the conditions that the curve has to go through the the root control point 778 and the bottom control point 775.

The meridian curves 771, 772 and 773 are determined for each of the control angles that divide 360 degrees around z-axis into a preset number of intervals. Then the points on the meridian curves at uniform z-increments are found. These points at each of the elevations are used to construct a cubic periodic hermite curve 779 around z-axis. Then each of these elevation curves such as curve 779 are evaluated for uniformly distributed preset number of points around the z axis. Thus using the grid of points generated by the elevation curves, meridian curves are used to generate the whole grid for the cutter.

The crown surface part can be generated relatively quickly as it is based on functions. The speed in drawing the crown surface allows real time shaping by the user when the user moves the crown control points and the top control points or when the user edits the gingival line. Also it facilitates the intersection finding itself as the system can rapidly determine whether a given point, such as a vertex of the tooth mesh, is inside or outside the gingival cutting surface.

The initial placement of the crown control points is done using an approximate tooth shape inferred from the tooth identification information (step 256 of FIG. 8A). For example for a molar these points should be farther away from z-axis than for an incisor. The root part of the gingival cutting surface is then generated (step 258). The root part can be made up of a parabolic surface at the bottom of the surface and a ruled surface that connects this parabolic surface to the crown surface.

Figure 9:
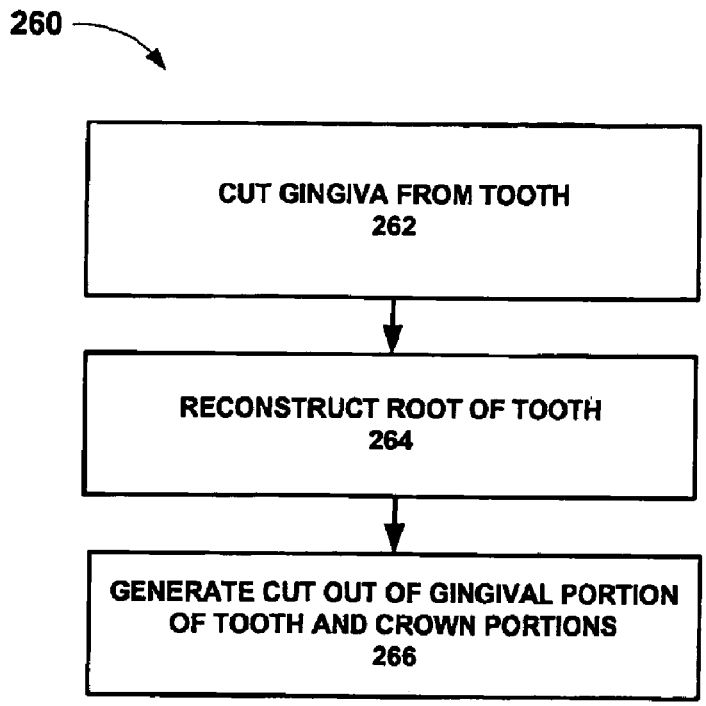
FIG. 9 is a flow chart illustrating usage of the gingival cutting surface to extract gingiva from the tooth.

FIG. 9 shows in more detail step 260 of FIG. 5 that uses the gingival cutting surface to extract gingival from the tooth. The input to the process of FIG. 9 is a triangular mesh model of the tooth and a triangular mesh model of the gingival cutting surface. The process of FIG. 9 generates a cutout gingival portion of the tooth and the crown portions (step 262). A curved clipping procedure is used to cut the gingiva from the tooth. The process then reconstructs a tooth root using gingival cutting surface (step 264). The reconstruction of the root happens as part of cutting process, and the root portion of the cut tooth will be part/whole of the root portion of the gingival cutting surface. The process then generates a cut-out of the gingival portion of the tooth and the crown portions (step 266).

Figure 10:
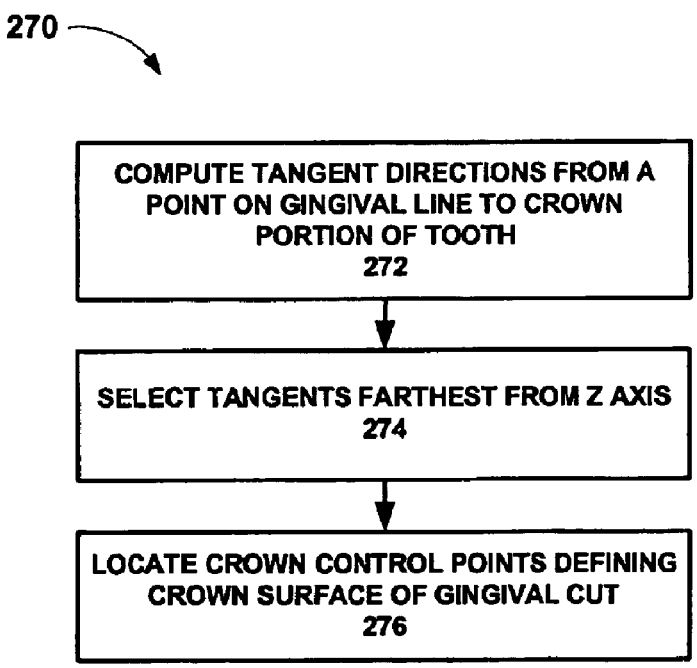
FIG. 10 is a flow chart illustrating creation of a compact crown portion of the gingival cut, yet doesn't cut through the crown portion of the tooth.
Figure 11:
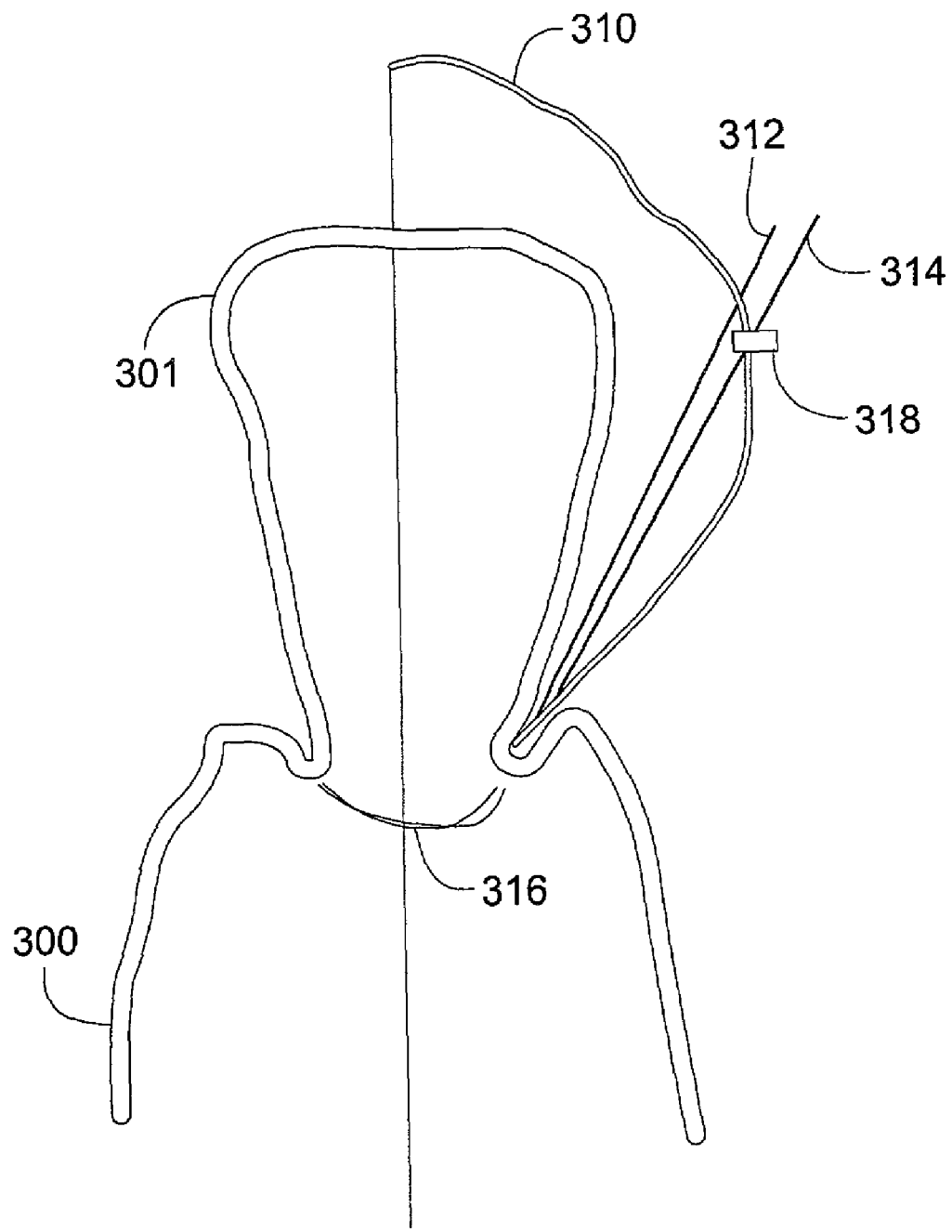
FIG. 11 shows one exemplary operation of the process of FIG. 10 on a tooth model.

In cases where the gingival line is deep, the crown surface constructed using tooth type information might cut through part of gingiva. For this purpose an "AutoCrown" procedure shown in FIG. 10 can be used. The process of FIG. 10 creates a compact crown portion of the gingival cut, yet it does not cut through the crown portion of the tooth. Turning now to FIG. 10, in each of the directions away from z-axis, the tangent directions are computed from the corresponding point on the gingival line to the crown portion of the tooth (step 272). These tangents are selected so that they are farthest from the z-Axis (step 274). In other words, this tangent does not intersect the crown portion of the gingival cut, but touches the crown portion at one or more points. FIG. 11 shows one particular (z, phi) plane. These tangents are used to automatically locate the crown control points that define the crown surface of the gingival cut (step 276).

FIG. 11 shows one exemplary operation of the process of FIG. 10 on a tooth model 301. The tooth model 301 rests above a gingiva 300. The tooth model 301 interfaces with the gingiva 300 at a gingival line 316. Further, a crown surface 310 covers the tooth 301. A tangent line 312 is projected from the gingival line 316 toward a corresponding point on the crown surface 310. The process of FIG. 11 computes an alternate tangent line 314 by shifting the tangent line 312 by a small offset. The intersection of the alternate tangent line 314 with the crown surface 310 is a new crown point 318 in accordance with the process of FIG. 10.

Figure 12:
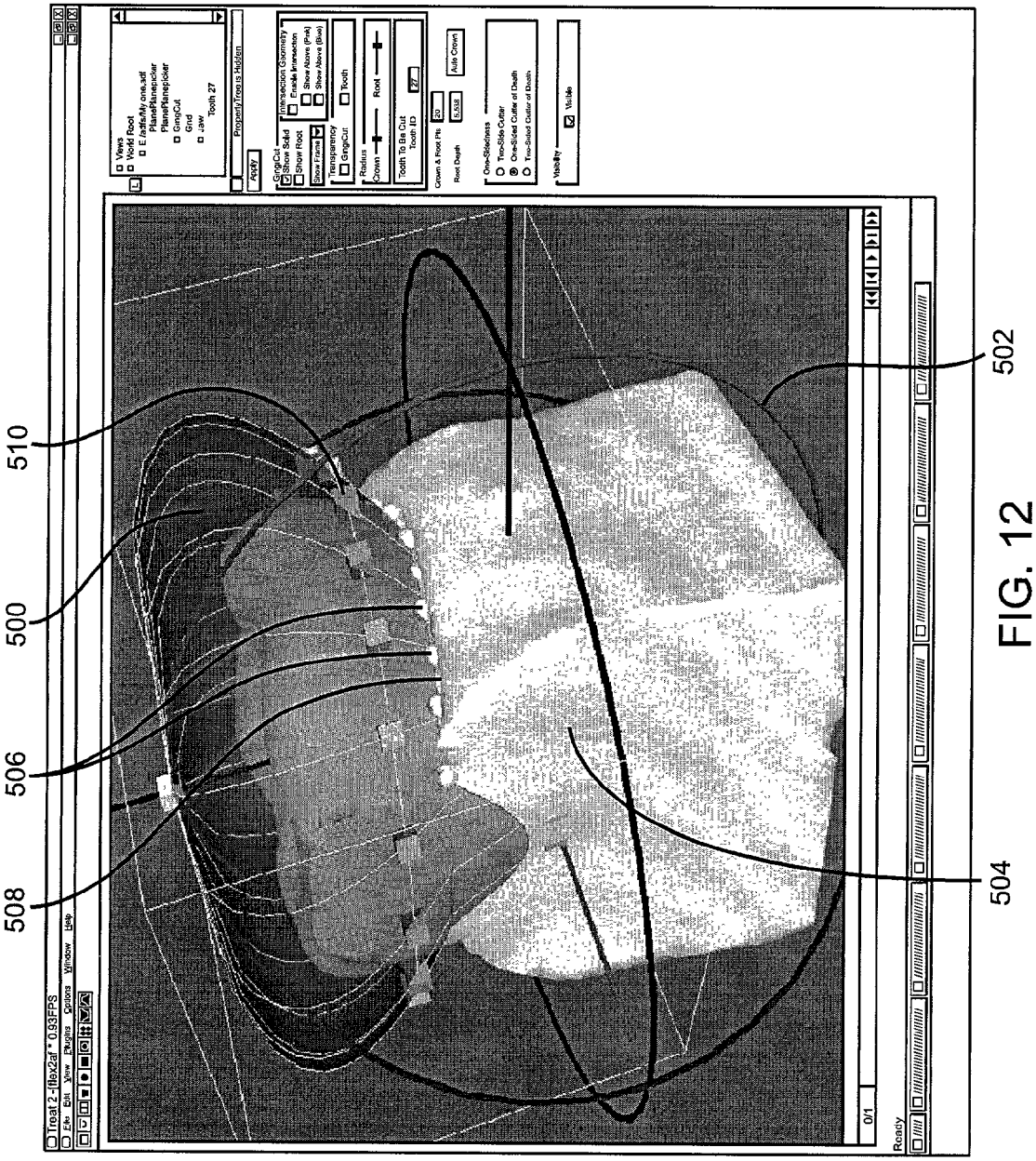
FIG. 12 shows an exemplary user interface for a cutter that can remove gingiva from a tooth model.

FIG. 12 shows an exemplary user interface for a cutter 500 that can remove gingiva 504 from a tooth model. The cutter 500 provides an axis widget 502 that allows a user to rotate and translate the cutter 500 in and around the three principal directions (x, y and z). Ball controls 506 are provided along a gingival line 508 so the user can edit the gingival line 508. Control cubes 510 are provided to allow the user to change the shape of the cutter 500 and these cubes 510 can be edited by moving them. All user changes will cause a recomputation of the surface of the cutter 500 and force the surface to pass through the gingival line 508.

The user interface allows the user to turn a solids option on and off so that the surface of the gingival cutter 500 can be visualized from its wire-frame model. The root can be displayed or can remain hidden using a transparency setting and is useful for visualizing the root structure inside the tooth. Intersection geometry can be shown, and the root and crown points and root depth can be specified.

Figure 13:
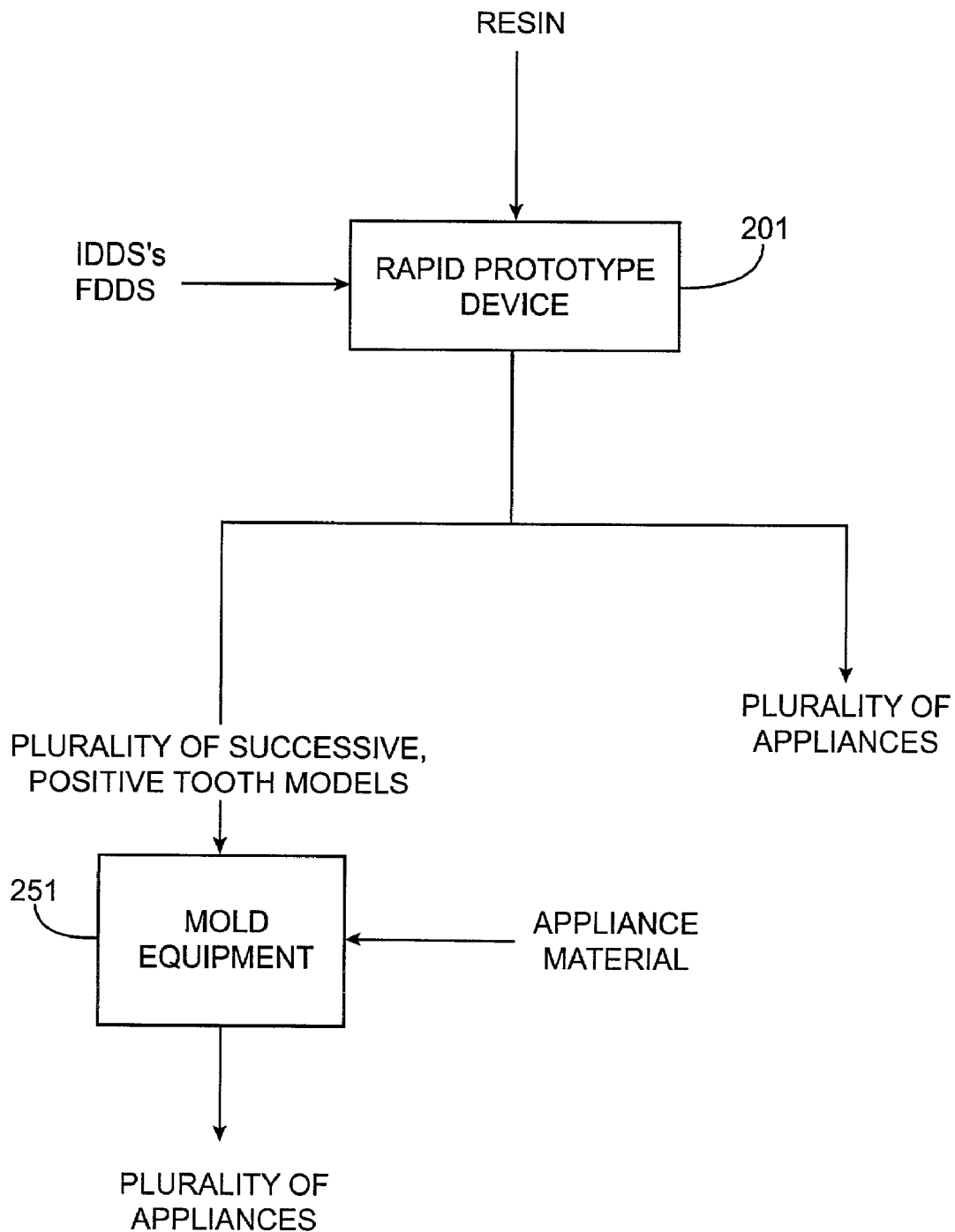
FIG. 13 is a diagram of a system for fabricating appliances.

Once the intermediate and final data sets have been created, the appliances may be fabricated as illustrated in FIG. 13. Common fabrication methods employ a rapid prototyping device 201 such as a stereolithography machine. A particularly suitable rapid prototyping machine is Model SLA-250/50 available from 3D System, Valencia, Calif. The rapid prototyping machine 201 selectively hardens a liquid or other non-hardened resin into a three-dimensional structure that can be separated from the remaining non-hardened resin, washed, and used either directly as the appliance or indirectly as a mold for producing the appliance. The prototyping machine 201 receives the individual digital data sets and produces one structure corresponding to each of the desired appliances. Generally, because the rapid prototyping machine 201 may utilize a resin having non-optimum mechanical properties and which may not be generally acceptable for patient use, the prototyping machine typically is used to produce molds that are, in effect, positive tooth models of each successive stage of the treatment. After the positive models are prepared, a conventional pressure or vacuum molding machine 251 is used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine 251 produces each of the appliances directly from the positive tooth model and the desired material. Suitable vacuum molding machines are available from Raintree Essix, Inc.

After production, the appliances can be supplied to the treating professional all at one time. The appliances are marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Because a patient's teeth may respond differently than originally expected, the treating clinician may wish to evaluate the patient's progress during the course of treatment. The system can also do this automatically, starting from the newly-measured in-course dentition. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few aligners, delaying production on subsequent aligners until the patient's progress has been evaluated.

Figure 14:
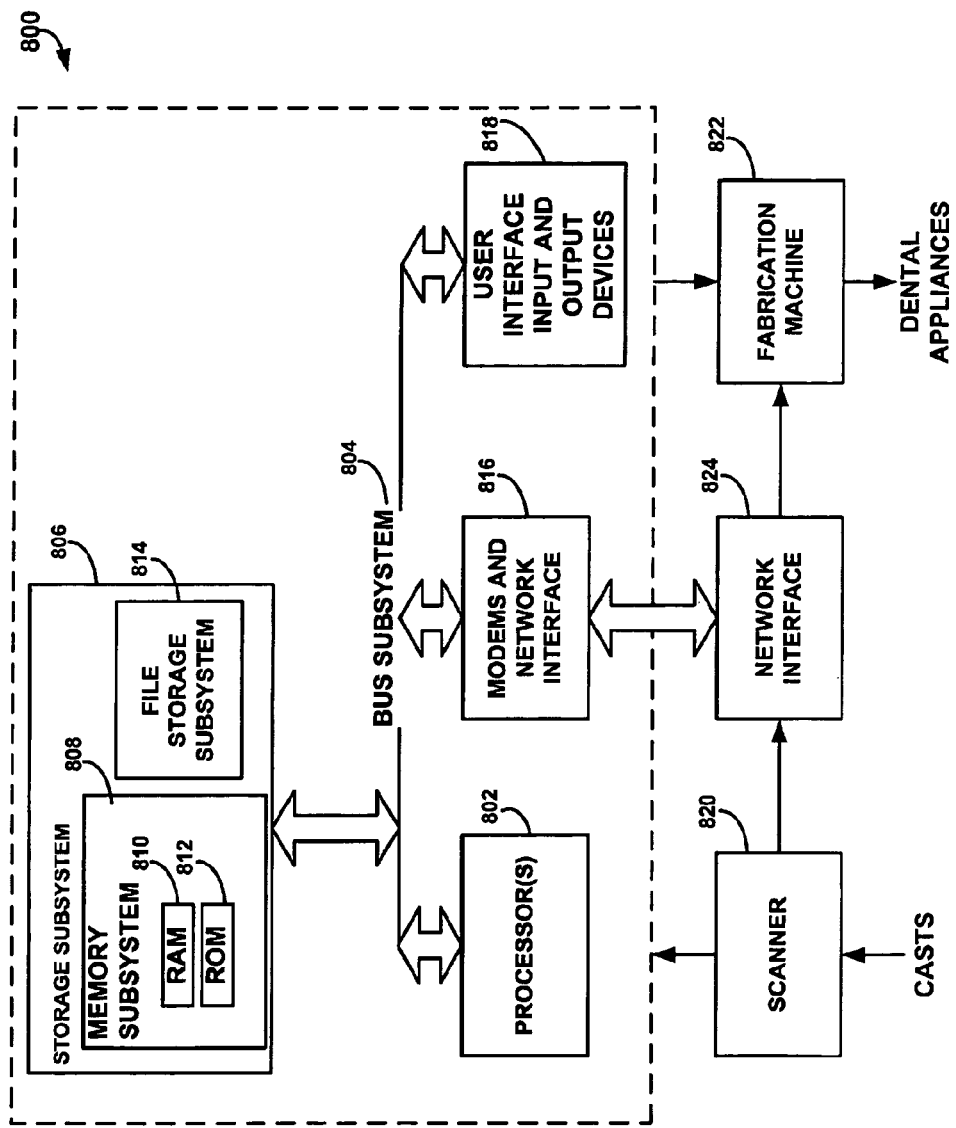
FIG. 14 is a diagram of a computer system supporting the manufacturing of appliances.

FIG. 14 is a simplified block diagram of a data processing system 800 that may be used to develop orthodontic treatment plans. The data processing system 800 typically includes at least one processor 802 that communicates with a number of peripheral devices via bus subsystem 804. These peripheral devices typically include a storage subsystem 806 (memory subsystem 808 and file storage subsystem 814), a set of user interface input and output devices 818, and an interface to outside networks 816, including the public switched telephone network. This interface is shown schematically as "Modems and Network Interface" block 816, and is coupled to corresponding interface devices in other data processing systems via communication network interface 824. Data processing system 800 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display, or a three dimensional pointing device, such as the gyroscopic pointing device described in U.S. Pat. No. 5,440,326, other types of user interface input devices, such as voice recognition systems, can also be used.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual display such as audio output.

Storage subsystem 806 maintains the basic required programming and data constructs. The program modules discussed above are typically stored in storage subsystem 806. Storage subsystem 806 typically comprises memory subsystem 808 and file storage subsystem 814.

Memory subsystem 808 typically includes a number of memories including a main random access memory (RAM) 810 for storage of instructions and data during program execution and a read only memory (ROM) 812 in which fixed instructions are stored. In the case of Macintosh-compatible personal computers the ROM would include portions of the operating system; in the case of IBM-compatible personal computers, this would include the BIOS (basic input/output system).

File storage subsystem 814 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or or wide-area network media, including telephone lines. Similarly, the input devices and display need not be at the same location as the processor, although it is anticipated that personal computers and workstations typically will be used.

Bus subsystem 804 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 820 is responsible for scanning casts of the patient's teeth obtained either from the patient or from an orthodontist and providing the scanned digital data set information to data processing system 800 for further processing. In a distributed environment, scanner 820 may be located at a remote location and communicate scanned digital data set information to data processing system 800 via network interface 824.

Fabrication machine 822 fabricates dental appliances based on intermediate and final data set information received from data processing system 800. In a distributed environment, fabrication machine 822 may be located at a remote location and receive data set information from data processing system 800 via network interface 824.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly. Moreover, the tooth models may be posted on a hypertext transfer protocol (http) web site for limited access by the corresponding patients and treating clinicians.

What is claimed is:

1. A computer-implemented method for separating a tooth from adjacent structure, comprising:
   identifying a line between the tooth and the adjacent structure;
   defining a closed cutting surface that passes through the line between the tooth and the adjacent structure and that creates an approximate shape of a root of the tooth; and
   applying the cutting surface between the tooth and the structure to separate the tooth from the structure in a single cut.

2. The method of claim 1, wherein the cutting surface is curved.

3. The method of claim 1, wherein the cutting surface is expressed as a function.

4. The method of claim 1, wherein the cutting surface is expressed as a spline function and a quadratic function.

5. The method of claim 1, wherein the cutting surface is expressed as a spline function and a parabolic function.

6. The method of claim 1, wherein the cutting surface is interactively adjusted.

7. The method of claim 4, wherein the interactive adjustment of the cutting surface modifies a function defining the cutting surface.

8. The method of claim 4, further comprising interactively highlighting the separated portion.

9. The method of claim 8, further comprising interactively highlighting the border of the separated portion.

10. The method of claim 1, wherein the cutting surface is defined by specifying a basis for the tooth.

11. The method of claim 1, wherein the structure is a gingiva, further comprising finding a line between a tooth surface and the gingiva and applying the cutting surface to said line.

12. The method of claim 11, further comprising finding a high curvature location on the tooth surface.

13. The method of claim 11, further comprising fitting a spline to the line.

14. The method of claim 1, wherein the cutting surface further comprises a plurality of surfaces.

15. The method of claim 14, wherein the root of the tooth is modeled as a parabolic surface below a gingival line.

16. The method of claim 14, further comprising defining an enclosing surface to enclose the crown of the tooth.

17. The method of claim 14, further comprising:
   displaying the surface specified with a plurality of nodes;
   adjusting one or more nodes to modify the surface; and
   applying the surface to separate the gingiva from the tooth.

18. The method of claim 17, further comprising providing a handle to adjust each orientation of the cutting shape.

19. The method of claim 17, wherein adjusting one or more nodes further comprises moving one or more nodes.

20. The method of claim 17, wherein the cutting surface is formed using a function in a cylindrical coordinate system.

21. A system for separating a tooth from adjacent structure, comprising:
   means for identifying a line between the tooth and the adjacent structure;
   means for defining a closed cutting surface that passes through the line between the tooth and the adjacent structure and that creates an approximate shape of a root of the tooth; and
   means for applying the cutting surface between the tooth and the structure to separate the tooth from the structure in a single cut.

22. A computer program, residing on a tangible storage medium, for use in separating a computer model of a tooth from a computer model of a dental structure, the program comprising executable instructions operable to cause a computer to:
   identify a line between the tooth and the structure;
   define a closed cutting surface that passes through the line between the tooth and the structure and that creates an approximate shape of a root of the tooth; and
   apply the cutting surface between the tooth and the structure to separate the tooth from the structure in a single cut,
   wherein applying the cutting surface includes reconstructing a root of the tooth.

23. A computer program, residing on a tangible storage medium, for use in separating a computer model of a tooth from a computer model of a dental structure, the program comprising executable instructions operable to cause a computer to:
   identify a line between the tooth and the structure;
   define a closed cutting surface that passes through the line between the tooth and the structure and that creates an approximate shape of a root of the tooth; and
   apply the cutting surface between the computer model of the tooth and the computer model of the dental structure to separate the computer model in a single cut.

24. A computer, comprising:
   a processor;
   a data storage device coupled to the processor, the data storage device containing code for use in separating a computer model of a tooth from a computer model of an adjacent dental structure, the program comprising executable instructions operable to cause a computer to:
   identify a line between the tooth and the structure;
   define a closed cutting surface that passes through the line between the tooth and the structure, wherein the cutting surface is expressed as a spline function and a quadratic function and wherein the cutting surface further comprises a plurality of surfaces and wherein the root of the tooth is modeled as a parabolic surface below a gingival line; and
   apply the cutting surface to the tooth to separate the tooth from the dental structure in a single cut.

25. The system of claim 24, further comprising instructions to define an enclosing surface to enclose the crown of the tooth.

* * * * *